US009738678B2

(12) United States Patent
Doncel et al.

(10) Patent No.: US 9,738,678 B2
(45) Date of Patent: Aug. 22, 2017

(54) SUBSTITUTED NUCLEOSIDE DERIVATIVES WITH ANTIVIRAL AND ANTIMICROBIAL PROPERTIES

(71) Applicants: Eastern Virginia Medical School, Norfolk, VA (US); Board of Governors for Higher Education, State of Rhode Island and Providence Plantations, Providence, RI (US)

(72) Inventors: Gustavo F. Doncel, Norfolk, VA (US); Keykavous Parang, Irvine, CA (US); Hitesh Kumar Agarwal, New York, NY (US)

(73) Assignees: Eastern Virginia Medical School, Norfolk, VA (US); Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 15/079,918

(22) Filed: Mar. 24, 2016

(65) Prior Publication Data
US 2016/0311843 A1  Oct. 27, 2016

Related U.S. Application Data

(63) Continuation of application No. 12/668,262, filed as application No. PCT/US2008/069571 on Jul. 9, 2008, now Pat. No. 9,296,776.

(60) Provisional application No. 60/929,683, filed on Jul. 9, 2007.

(51) Int. Cl.
*C07H 19/06* (2006.01)
*C07D 411/04* (2006.01)
*C07H 19/10* (2006.01)
*C07H 19/16* (2006.01)
*C07H 19/20* (2006.01)

(52) U.S. Cl.
CPC .......... *C07H 19/06* (2013.01); *C07D 411/04* (2013.01); *C07H 19/10* (2013.01); *C07H 19/16* (2013.01); *C07H 19/20* (2013.01)

(58) Field of Classification Search
None
See application file for complete search history.

(56) References Cited

U.S. PATENT DOCUMENTS

| 5,026,688 | A | 6/1991 | Agrawal |
| 5,210,085 | A | 5/1993 | Liotta et al. |
| 5,512,671 | A | 4/1996 | Piantadosi et al. |
| 6,025,343 | A | 2/2000 | Herrmann et al. |
| 6,113,920 | A | * | 9/2000 | Maye | ................ | A61K 31/7072 424/400 |
| 7,807,677 | B2 | 10/2010 | Ekegren et al. |

| 2003/0003652 | A1 | 1/2003 | Gobel et al. |
| 2003/0036528 | A1 | 2/2003 | Gosselin et al. |
| 2004/0077554 | A1 | 4/2004 | Xu et al. |
| 2005/0119200 | A1 | 6/2005 | Roberts et al. |
| 2005/0119286 | A1 | 6/2005 | Otto et al. |
| 2005/0227933 | A1 | 10/2005 | Benkovic et al. |
| 2005/0267051 | A1 | 12/2005 | Lee et al. |
| 2006/0106044 | A1 | 5/2006 | Sommadossi et al. |
| 2007/0025964 | A1 | 2/2007 | Schinazi et al. |

FOREIGN PATENT DOCUMENTS

| CN | 1817866 | 8/2006 |
| DE | 4324450 | 1/1995 |
| EP | 0056265 A2 | 7/1982 |
| EP | 0393920 A2 | 10/1990 |
| EP | 0524796 A1 | 1/1993 |
| FR | 2794753 | 12/2000 |
| GB | 2260319 A | 4/1993 |
| WO | WO-9000555 A1 | 1/1990 |
| WO | WO-91/15488 A1 | 10/1991 |
| WO | WO-9500177 A1 | 1/1995 |
| WO | WO-95/05199 | 2/1995 |
| WO | WO-9532984 A1 | 12/1995 |
| WO | WO-9730052 A1 | 8/1997 |
| WO | WO-9843972 | 10/1998 |
| WO | WO-02088159 A1 | 11/2002 |
| WO | WO-2005/049633 A1 | 6/2005 |
| WO | WO-2005111056 A1 | 11/2005 |

(Continued)

OTHER PUBLICATIONS

Aggarwal et al. "Synthesis and biological evaluation of prodrugs of zidovudine." J. Med. Chem., vol. 33, pp. 1505-1510 (1990).
Besada et. al, "Nucleoside Prodrugs of A3 Adenosine Receptor Agonists and Antagonists," Collection of Czechoslovak Chemical Communications, vol. 71, No. 6, pp. 912-928 (2006).
Carteau et al., "Inhibitory effect of the polyanionic drug suramin on the in vitro HIV DNA integration Reaction," Archives of Biochemistry and Biophysics, vol. 305, pp. 606-610 (Sep. 1, 1993).
Chu et al., "Brain targeting of anti- HIV nucleosides: synthesis and in vitro and in vivo studies of dihydropyridine derivatives of 3'-azido-2',3'-dideoxyuridine and 3'-azido-3'-deoxythymidine," J. Med. Chem., vol. 33, pp. 2188-2192 (1990).
D'Cruz et al., "Aryl phosphate derivatives of Bromo-Methoxy-Azidothymidine are dual-function spermicides with potent anti-Human Immunodeficiency Virus," Biology of Reproduction, vol. 59, pp. 503-515 (1998).

(Continued)

Primary Examiner — Traviss C McIntosh, III
(74) Attorney, Agent, or Firm — Wilmer Cutler Pickering Hale and Dorr LLP

(57) ABSTRACT

The present invention relates to fatty acid and fatty alcohol substituted nucleoside derivatives and nucleoside and nucleoside derivatives substituted on multivalent scaffolds (e.g., polymers, peptides, polycarboxylic acid substituted compounds, compounds containing polycycloSaligenyl groups) that display potent anti-HIV activity. Furthermore, they show enhanced activity against multi-drug resistant, R5, and cell-associated virus. Some of them also display activity against other sexually transmitted pathogens and sperm. The present invention provides their methods of synthesis, composition of matter, and methods of use. Emphasis is placed on their application as topical microbicides to treat or prevent sexual transmission of disease, especially HIV/AIDS.

14 Claims, 33 Drawing Sheets

(56) References Cited

FOREIGN PATENT DOCUMENTS

| WO | WO-2006/030217 A2 | 3/2006 |
|---|---|---|
| WO | WO-2006/074925 A1 | 7/2006 |
| WO | WO-2007/121918 A2 | 11/2007 |
| WO | WO-2007/121919 A1 | 11/2007 |
| WO | WO-2007/121920 A2 | 11/2007 |

OTHER PUBLICATIONS

Dessolin et al., "New Bicyclam-AZT conjugates: design, synthesis, anti-HIV evaluation, and their interaction with CXCR-4 coreceptor." J. Med. Chem., vol. 42, pp. 229-241 (1999).
Dezutti et al., "In vitro comparison of topical microbicides for prevention of human Immunodeficiency virus type 1 transmission," Antimicrobial Agents and Chemotherapy, vol. 48, No. 10, vol. 3834-3844 (2004).
Doncel et al., "Vaginal microbicides: a novel approach to preventing sexual transmission of HIV," Current HIV/AIDS Reports, vol. 1, pp. 25-32 (2004).
Fridkin et al., "tUFTSIN-AZT conjugate: potential macrophabe targeting for AIDS therapy," Journal of peptide science, vol. 11, pp. 37-44 (Jan. 1, 2005).
Gao et al., "Synthesis of azidothymidine-bound sulfated alkyl oligosaccharides and their inhibitory effects on AIDS virus infection in vitro," Polymer J., vol. 30 pp. 243-248 (1998).
Gao et al., "Synthesis, enzymatic hydrolysis, and anti-HIV activity of AZT-spacer-curdlan sulfates," Macromolecules, vol. 32, pp. 8319-8324 (1999).
International Search Report for International Patent Application No. PCT/US08/69571 dated Dec. 16, 2008 (4 pages).
Kawaguchi et al., "Ester prodrugs of zidovudine." Journal of Pharmaceutical Sciences, vol. 79, pp. 531-533 (1990).
Kryczka et al., "Two novel nucleoside ester derivatives of chlorambucil as potential antileukemic prodrugs: a preliminary study," Anti-Cancer Drugs, vol. 18, No. 3, pp. 301-310 (2007).
Langner et al., "Oxatetradecanoic acid is fungicidal for Cryptococcus neoformans and inhibits replication of human immunodeficiency virus I," the Journal of Biological Chemistry, vol. 267, No. 24, pp. 17159-17169 (1992).
Ledermann et al., "Microbicides and other topical strategies to prevent vaginal transmission of HIV." Nature Reviews, Immunology, vol. 6, pp. 371-382 ( May 2006).
Marquez et al., "Carbocyclic Nucleosides", Medicinal Research Reviews, vol. 6, No. 1, pp. 1-40 (1986).
Marquez et al., "Experimental and Structural Evidence that Herpes 1 Kinase and Cellular DNA Polymerase(s) Discriminate on the Basis of Sugar Pucker," J. Am. Chem. Soc. vol. 126, No. 2, pp. 543-549 (2004).
Martin, "Remington, The Science and Practice of Pharmacy," Mack Publishing Company, 19th Edition Easton, PA, (1995).
Moulard et al., "Selective interations of polyanions with basic surfaces on Human Immunodeficiency Virus Type 1 gp120," Journal of Virology, vol. 74, No. 4, pp. 1948-1960 (Feb. 2000).
Palomino et al., "Synthesis and in vitro evaluation of some modified 4-thiopyrimidine nucleosides for prevention or reversal of AIDS—associated neurological disorders," J. Med. Chem., vol. 33, pp. 258-263 (1990).
Parang et al., "Synthesis, in vitro anti-HIV structure-activity relationships and stability of 5'-O-myristoyl analogue derivatives of 3'-azido-2',3'-dideoxythymidine as potential prodrugs of 3'-azido-2',3'-dideoxythymidine (AZT) as potential prodrugs," Antiviral Chemistry and Chemotherapy, vol. 9, pp. 311-323 (1998).
Parang et al., "Synthesis, in vitro anti-HIV activity, and biological stability of 5'-O-myristoyl analog derivatives of 3'-fluoro-2',3'-dideoxythymidine (FLT) as potential bifunctional prodrugs of FLT," Nucleosides & Nucleotides, vol. 17, pp. 987-1008 (1998).
Scordi-Bello et al., "Candidate sulfonated and sulfated topical microbicides: Comparison of anti-human immunodeficiency Virus activities and mechanisms of action," Antimicrobial agents and Chemotherapy, vol. 49, pp. 3607-3615 (Sep. 1, 2005).
Seki et al., "Enhanced delivery of zidovudine through rat and human skin via ester prodrugs," Pharmaceutical Research, vol. 7, No. 9, pp. 948-952 (1990).
Sharma et al., "Synthesis and anti-HIV activity of prodrugs of azidothymidine," Antiviral Chemistry and Chemotherapy, vol. 4, No. 2, pp. 93-96 (1996).
Solas et al., "Intracellular nucleotides of (-)-2',3'-deoxy-3'-thiacytidine in peripheral blood mononuclear cells of a patient infected with human immunodeficiency virus," Antimicrobial Agents and Chemotherapy, vol. 42, No. 11, pp. 2989-2995 (Nov. 1998).
Supplementary European Search Report issued by the European Patent Office for Application No. 08796131.4 dated Aug. 20, 2012 (13 pages).
Tadayoni et al., "Synthesis, in vitro kinetics, and in vivo studies on protein conjugates of AZT: evaluation as a transport system to increase brain delivery," Bioconjugate Chemistry, ACS, vol. 4, pp. 139-145 (Mar. 1, 1993).
Torrence et al., "Synthesis and pharmacokinetics of a dihydropyridine chemical delivery system for the antiimmunodeficiency virus agent, dideoxycytidine," J. Med. Chem., vol. 36, pp. 529-537 (1993).
Tsuzuki et al., "Adamantane as a brain-directed drug carrier for poorly absorbed drug. 2. AZT derivatives conjugated with the 1-adamantane moiety," Journal of Pharmaceutical Sciences, vol. 83, No. 4, pp. 481-484 (1994).
Tuchnaya et al., "Synthesis of anti-HIV nucleoside conjugates with lipophilic diol compounds," Pharmaceutical Chemistry Journal, vol. 40, pp. 276-280 (May 1, 2006).
Universitat Hamburg, "Stereoselective Syntheses of Potentially Antivirally Active Carbocyclic Nucleosides", retrieved online from URL: www.chemie.uni-hamburg.de/oc/mejer/research/carbocyclic.html, Jan. 28, 2015, pp. 1-5.
Vlieghe et al., "Synthesis of new covalently bound k-carrageenan-AZT conjugates with improved anti-HIV activities," J. Med. Chem., vol. 45, pp. 1275-1283 (2002).
Xie et al., "Phosphatidyl-2',3'-dideoxy-3'-thiacytidine: synthesis and antiviral activity in hepatitis B-and HIV-1-infected cells," Antiviral Research, vol. 28, pp. 113-120 (1995).
Zahran M. A., et al., "The potential of aspirin in pro-drug synthesis. A new potential delivery system of AZT and FLT," Arc. Pharm. Pharm. Med. Chem., vol. 329, pp. 417-420 (1996).
Zhang et al., "A New Class of 5-Fluoro-2'-deoxyuridine Prodrugs Conjugated with a TumorHoming Cyclic Peptide CNGRC by Ester Linkers: Synthesis, Reactivity, and Tumor-Cell-Selective Cytotoxicity," Pharmaceutical Research, vol. 22, Issue: 3, pp. 381-389 (2005).
Camplo et al., "Synthesis and biological evaluation of polyaminated 2',3'-dideoxy-3'-thiacytidine prodrugs," Nucleosides & Nucleotides, 18/4-5, pp. 879-880 (1999).
Chimalakonda et al., "Synthesis, Analysis, in Vitro Characterization, and in Vivo Disposition of a Lamivudine-Dextran Conjugate for Selective Antiviral Delivery to the Liver," Bioconj. Chem., 18(6), pp. 2097-2108 (2007).
Xue et al., "Preparation of lamivudyl palmitate solid lipid nanoparticles"; J Fourth Mil Med Univ 24(10), pp. 890-892 (2003).
Office Action issued in corresponding Canadian Patent Application No. 2,717,788 on Nov. 2, 2016 (6 pages).
Office Action issued in corresponding Indian Patent Application No. 86/CHENP/2010 on Jan. 9, 2017 (10 pages).
Hoong et al., "Enzyme-mediated enantioselective preparation of pure enantiomers of the antiviral agent 2',3'-dideoxy-5-fluoro-3'-thiacytidine (FTC) and related compounds," J. Org. Chem., 57(21), 5563-5565 (1992).

* cited by examiner

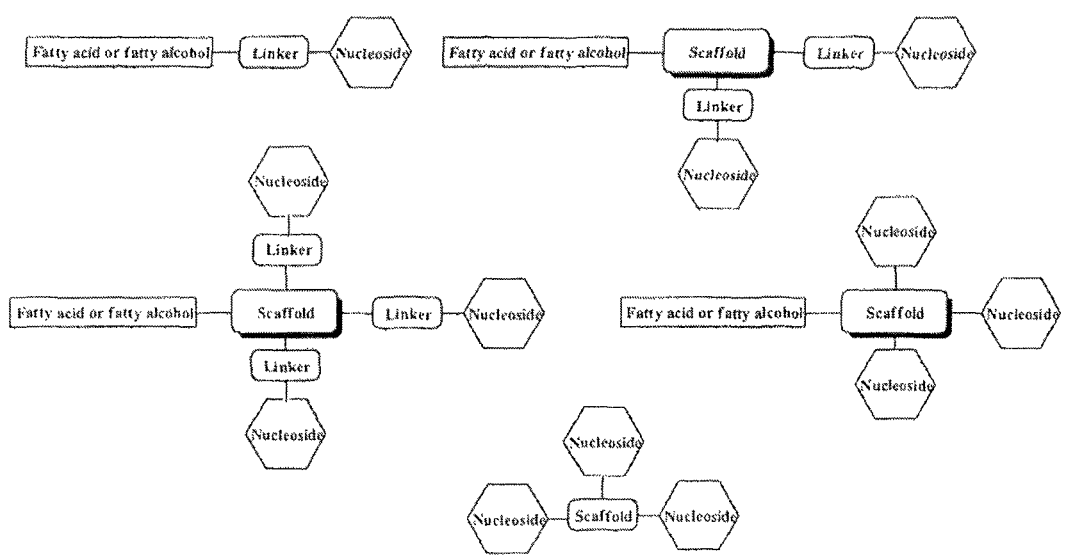
FIG. 1 General format of conjugation between nucleosides, linker, fatty acids or fatty alcohols, and scaffolds

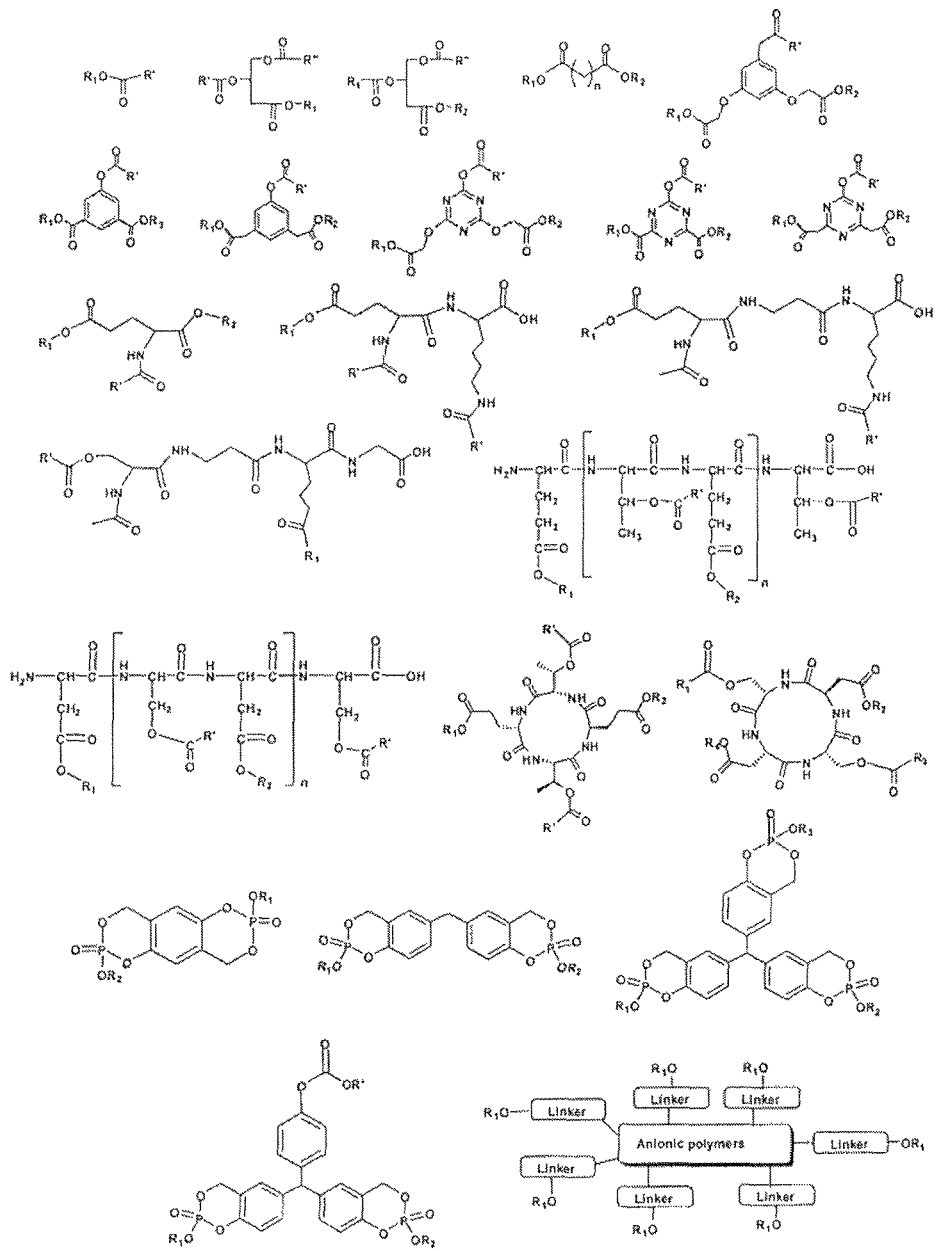
FIG. 2 General chemical structures of some of nucleoside-fatty acid, nucleoside-fatty alcohol, multivalent scaffold-nucleoside conjugates.

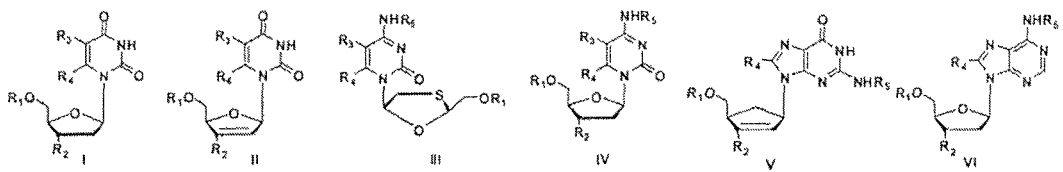
FIG. 3A Chemical structures of the compounds (Formulas I-VI).

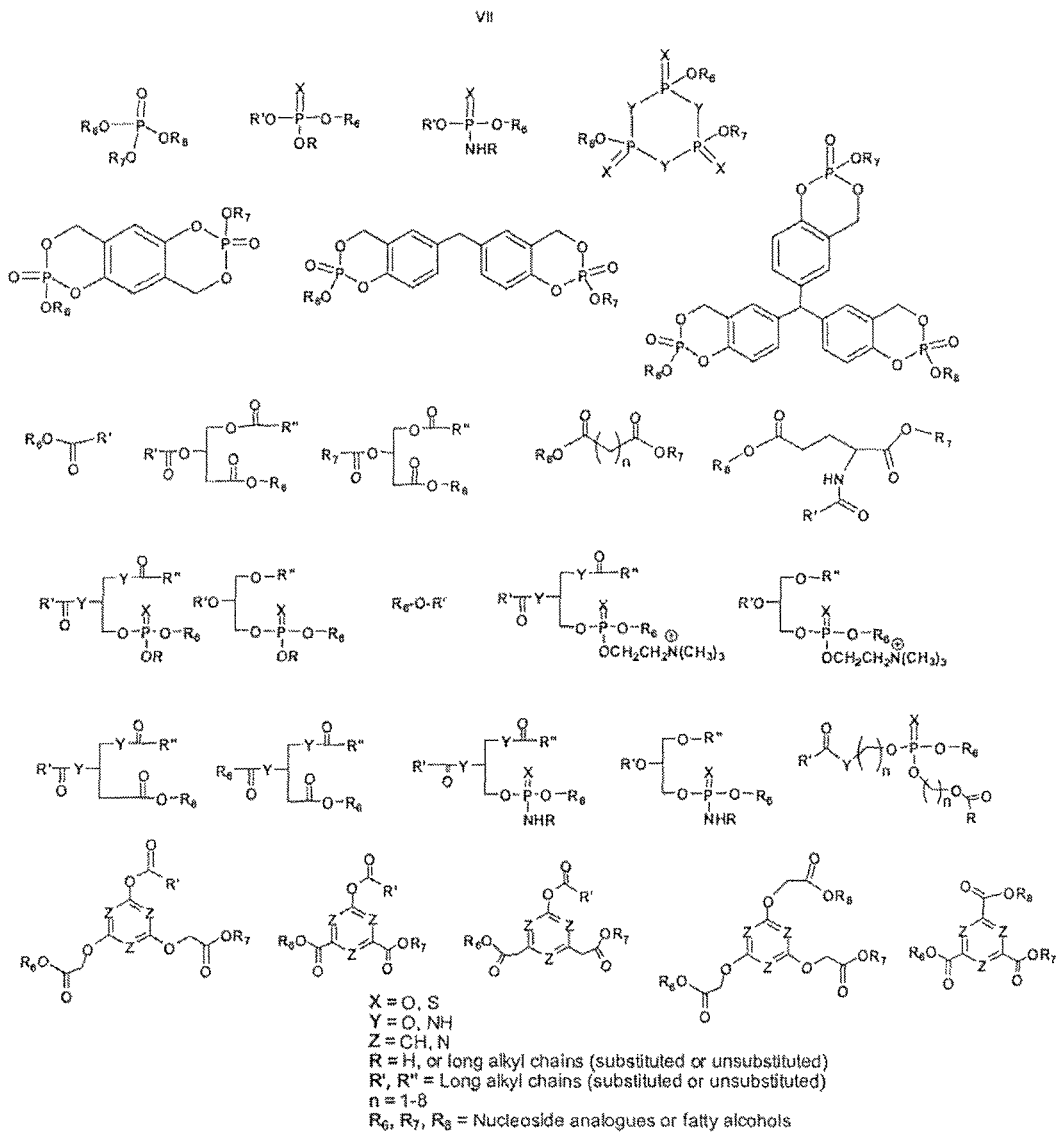
FIG. 3B Chemical structures of the compounds (Formula VII).

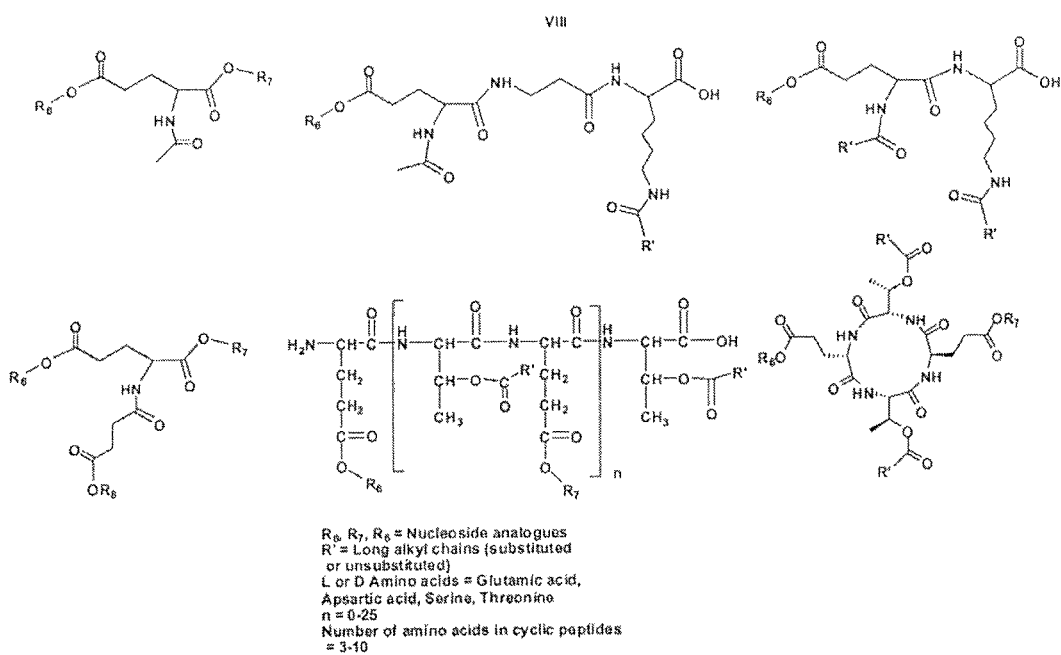
FIG. 3C Chemical structures of the compounds (Formula VIII).

KPH-1.7; R = F
KPH-1.8; R = N₃

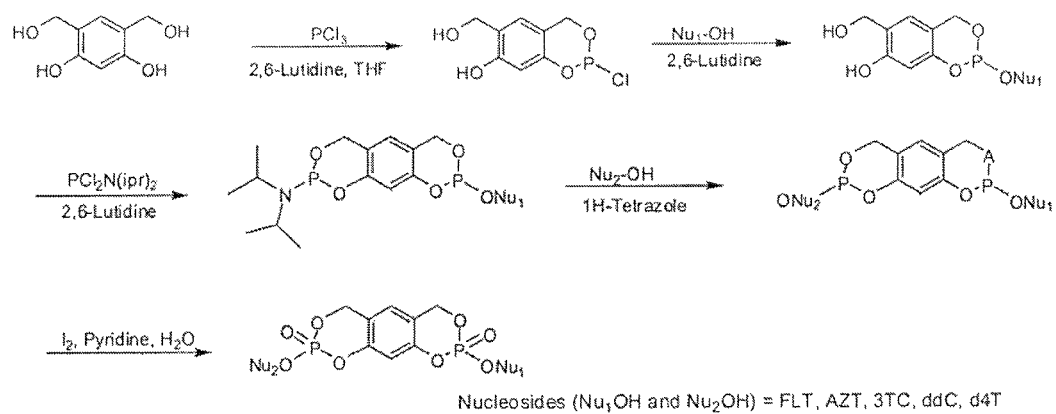
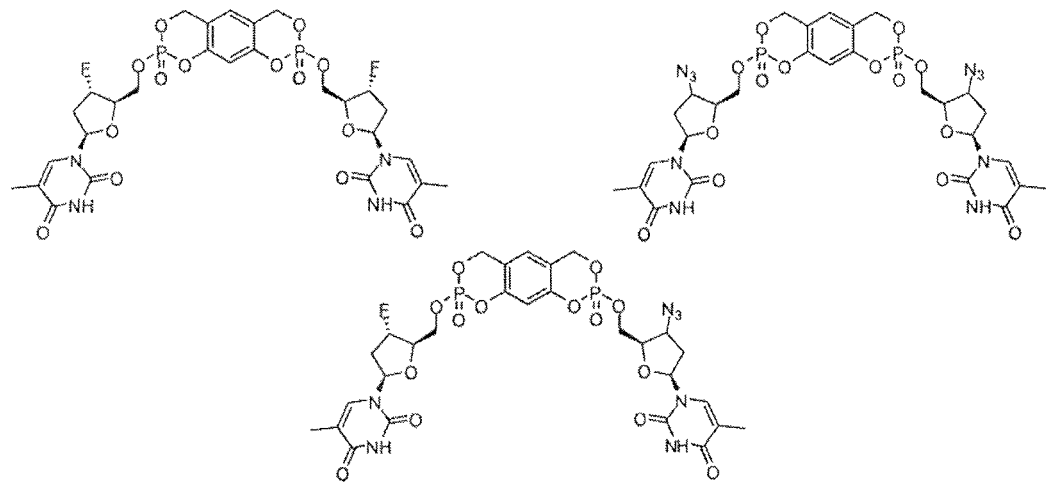
FIG. 28

SUBSTITUTED NUCLEOSIDE DERIVATIVES WITH ANTIVIRAL AND ANTIMICROBIAL PROPERTIES

STATEMENT AS TO RIGHTS TO INVENTIONS MADE UNDER FEDERALLY SPONSORED RESEARCH AND DEVELOPMENT

The present invention is supported in part by the CONRAD program (HRN-A-00-98-00020-00), administered under a cooperative agreement between the U.S. Agency for International Development (USAID) and Eastern Virginia Medical School. The government may have certain rights in this invention.

FIELD OF THE INVENTION

The invention generally relates to fatty acid or fatty alcohol substituted nucleoside derivatives and nucleoside and nucleoside derivatives substituted on multivalent scaffolds (e.g., polymers, peptides, polycarboxylic acid substituted compounds, compounds containing polycycloSaligenyl groups) that display activity against HIV and other sexually transmitted pathogens. These agents may be used systemically as therapeutic or preventative agents, or as topical microbicides used to treat, prevent or reduce sexual transmission of infectious diseases, in particular, HIV/AIDS.

BACKGROUND OF THE INVENTION

The increasing prevalence of sexually transmitted diseases (STDs) is a serious public health problem affecting both developing resource-constrained countries. In the latter, the acquired immunodeficiency syndrome (AIDS) epidemic is taking a devastating toll in human lives. According to the World Health Organization, almost 40 million people were living with HIV at the end of 2006, a year in which 4.3 million people were newly infected and 2.9 million died of AIDS-related diseases. Most new infections are occurring in the developing world, where women are most vulnerable. In sub-Saharan Africa, for example, 57% of people living with HIV are women, and young women between 15 and 24 years old are at least three times more likely to be HIV positive than young men.

There are no candidate vaccines in the pipeline that can induce sterilizing immunity and protect against infection with HIV. Therefore, there is an urgent need to develop additional safe and effective preventative strategies. One of those strategies has become known as microbicides, topically applied agents that prevent or reduce transmission of infectious disease, in particular HIV/AIDS (Lederman, M. M and Offord, R. E, Hartley, O. *Nat Rev Immunol.* 2006. 6: 371-382).

According to their mechanism of action, the microbicide pipeline contains virucides (i.e., compounds that directly inactivate or destroy the virus), entry inhibitors, replication inhibitors, and integration and post-integration inhibitors (Doncel, G. and Mauck, C. *Curr HIV/AIDS Rep.* 2004. 1: 25-32). Within the replication or reverse transcriptase inhibitors (RTIs), there are only a few, namely, UC-781 (Thiocarboxanilide), TMC-120 (Dapivirine) and MIV-150 (N-(5-cyano-2-pyridinyl)-N'-[1S,2S)-2-[6-fluoro-2-hydroxy-3-(1-oxopropyl)phenyl]cyclopropyl] urea) all non-nucleoside RTIs, and PMPA (Tenofovir), a nucleotide analogue. Although they are the most potent microbicides in development, these agents, especially the non-nucleosides, have poor water solubility and high susceptibility to induce resistant virus. In part, this is due to the fact that they act through a very specific, but single mechanism of action. They are also less effective against cell-associated virus.

Another factor that compounds the problem of fighting the epidemic is the continued development of drug-resistant virus. New and more potent anti-HIV agents are constantly needed as existing therapies succumb to newly developed resistant virus.

BRIEF SUMMARY OF THE INVENTION

The present invention relates to novel nucleoside derivatives and nucleoside conjugates. The compounds and compositions of the invention may be used systemically as therapeutic or preventative agents or topically as microbicides that display potent anti-HIV activity, including against multi-drug resistant virus and cell-associated virus, as well as antimicrobial activity against certain STD pathogens.

Besides displaying antiviral cooperative effects, the compounds and compositions of the invention offer an increased genetic barrier to resistance, reduced toxicity, and ease of formulation for topical microbicidal applications. 12-Azidododecanoyl and 12-thioethyldodecanoyl derivatives of the nucleosides are exemplary anti-HIV and microbicidal agents. These fatty acids may be connected in different ways to 3'-fluoro-2',3'-deoxythymidine (FLT), 2',3'-dideoxy-3'-thiacytidine (lamivudine, 3TC), 2',3'-didehydro-2',3'-dideoxythymidine (stavudine, d4T), 2',3'-dideoxy-5-fluoro-3'-thiacytidine (emtricitabine, FTC), 2',3'-dideoxycytidine (zalcitabine, ddC), 3'-azido-3' deoxythymidine (zidovudine, AZT), and tenofovir (FIG. 2).

In addition to direct ester derivatives, the fatty acids or fatty alcohols are linked to the nucleosides through other linkers and/or scaffolds, including phosphoramidate, phosphotriesters, phosphodiesters, phosphomonoesters, triglycerides, linear peptide backbones, cyclic peptide backbone, hydroxyphenyldicarboxylic acid derivatives, and compounds containing multi cycloSaligenyl groups. Linear and cyclic peptides can have glutamic acid or aspartic acid for the attachment of nucleosides and serine or threonine for the attachment of fatty acids. The number of amino acids can be of an desired length, preferably 1-25. Amino acids can be L or D. Polycarboxylic acid derivatives used as scaffolds for nucleosides conjugation include tribenzenetriacetic acid, hydroxybenzendicarboxylic acid, [(hydroxyphenylene)dixoy]diacetic acid, tris(carboxymethoxy)benzene, (triazinetriyltroxy)triacetic acid, triazine-tricarboxylic acid derivatives, such as (triazinetriyltroxy)triacetic acid and 1,3,5-triazine-2,4,6-tricarboxylic acid. Scaffolds containing one to three 2-hydroxybenzyl alcohol are conjugated through a phosphotriester (cycloSaligenyl phosphotriester) to nucleosides and/or fatty alcohols.

Exemplary fatty acid derivatives are attached directly to FTC, 3TC, d4T, ddC, AZT, and FLT through an ester bond as microbicidal agents. FTC, 3TC, d4T, ddC, AZT, and FLT derivatives attached through linkers to fatty acids or fatty alcohols, such as 12-azidododecanoyl and 12-thiododecanoyl derivatives, are contemplated anti-HIV and microbicidal agents. In an aspect, the invention is related to development of multivalent-nucleoside conjugates, such as novel polyanionic derivatives of nucleosides, peptide derivatives of nucleosides, small chemical scaffolds containing polycarboxylic acids conjugated to nucleosides, and 2-hydroxybenzyl alcohol-nucleoside phosphodiester conjugates (cycloSaligenyl-nucleoside conjugates). The present invention is directed to these and other important ends.

According to an aspect, the present invention provides compounds that are substituted with one or more nucleosides, nucleotides or nucleoside(tide) derivatives wherein one of its substitutions may be a long-chain fatty acid or fatty alcohol, which may be attached directly or indirectly through a linker or scaffold to the nucleoside/tide as shown in Formulas I-VIII (FIGS. 3A-C).

The nucleoside analogues in Formulas I-VIII may, in exemplary aspects, be pyrimidine derivatives based on the structures of 3'-deoxythymidine, 3'-deoxyuridine, 3'-deoxycytidine, 3-thiacytidine, their stereoisomers, their modified forms with substitutions at positions 5, 6, and substitutions at positions 1', 2', 3', 4', and 5' of carbohydrate moiety, purine nucleosides based on the structures of 3'-deoxyguanidine, 3'-deoxyadenosine, their modified forms with substitutions at positions 2, 4, 6, 8, and/or N4 of base moiety, substitutions at positions 2', 3', and 5' of carbohydrate moiety, and/or double bond between C3' and C4' in carbohydrate moiety or other nucleoside derivatives known to those skilled in the art.

In another aspect, the nucleoside derivative in Formulas I-VIII may be 3'-azido-3'deoxythymidine (AZT), 3'-fluoro-3'-deoxythymidine (FLT), 2', 3'-dideoxy-3'-thiacytidine (3TC), 2',3'-dideoxy-didehydro-2',3'-deoxythymidine (d4T), 2',3'-dideoxycytidine (ddC), or (−)-β-2',3-dideoxy-5-fluoro-3'-thiacytidine (FTC).

In another aspect, the nucleotide derivative in Formulas I-VIII may be a pyrimidine derivative based on the structures of 3'-deoxythymidine, 3'-deoxyuridine, 3'-deoxycytidine, 3-thiacytidine, their stereoisomers, their modified forms with substitutions at positions 5, 6, and substitutions at positions 1', 2', 3', 4', and 5' of carbohydrate moiety, purine nucleosides based on the structures of 3'-deoxyguanidine, 3'-deoxyadenosine, their modified forms with substitutions at positions 2, 4, 6, 8, and/or N4 of base moiety, substitutions at positions 2', 3', and 5' of carbohydrate moiety, and/or double bond between C3' and C4' in carbohydrate moiety or other nucleoside derivatives known to those skilled in the art, attached to a phosphate group as phosphomonoester, phosphodiester, phosphotriester, cyclic phosphotriester, cyclic phosphite triester, or phosphoramidate triester.

In another aspect, the fatty acid in Formulas I-VIII may be of the general formula $X(CH_2)_nY(CH_2)_nCOOH$ or $CH_3(CH_2)_nCH(Br)COOH$ and the fatty alcohol is $X(CH_2)_nY(CH_2)_nCH_2OH$ or $CH_3(CH_2)_nCH(Br)CH_2OH$, wherein n=0-18; $X=CH_3$, $N_3$, alkyl-S, alkyl-O, aryl-O, aryl-S, alkyl-NH, aryl-NH, Br, Cl, F, I, OH, $NH_2$, COOH, CHO, $CH_3S$, aryl, heteroaryl, phenyl, alkene, alkyne, or substituted phenyl; and $Y=CH_2$, O, S, NH, or 1,2,3-triazole.

Scaffolds are defined as skeleton, core, or template of the structure to which multiple functional groups and moieties may be attached. The scaffolds may have multiple positions for multivalent linkages. Non-limiting exemplary scaffolds may be polymers or smaller molecules containing several functional groups (e.g., hydroxyl, amino, or carboxylic acid groups) for attaching to other compounds. Scaffolds may be directly or indirectly attached through linkers to active components of the conjugates, such as nucleosides or nucleoside derivatives. Scaffolds are preferably able to attach more than two molecules directly or indirectly through linkers or spacers.

Linkers or spacers are flexible or rigid moieties which may be used to attach the scaffolds to functional groups and substituents of the conjugates, such as nucleosides or nucleoside derivatives, or to connect directly two or more active components, such as several nucleosides or nucleoside derivatives. In another aspect, the linker in Formulas I-VIII may be alkyl and/or aryl chains with different lengths, phosphoglycerate, phosphoramidate, phosphomonoester, phosphodiester, phosphotriester, cyclic phosphotriesters, cyclic phosphite triesters, 2-hydroxybenzyl alcohol, cycloSaligenyl groups, acetate, dicarboxylic acid esters (—OOC—$(CH_2)_n$COO—, n=0-14 such as succinate or suberate), L or D-amino acyl (—NH—$(CHR)_n$—CO—, R=H or side chains of amino acids, n=1-25 such as γ-aminobutyric acid, glutamic acid, aspartic acid, serine, threonine forming linear or cyclic peptides), polyethers (e.g., ethylene glycol ethers (—$OCH_2CH_2O)_n$—, n=1-14), carboxylic acid esters ethers (—OOC—$(CH_2)_n$—$CH_2O$—, n=0-14), polyamides, or any combination of the linkers.

In another aspect, the scaffold in Formulas I-VIII may be derivatives containing one to three 2-hydroxybenzyl alcohol (e.g., 4,4'-dihydroxy-3,3'-di-(hydroxymethyl)diphenylmethane, 4,6-dihydroxy-1,3-benzenedimethanol, 4,4',4''-methanetriyltris(2-(hydroxymethyl)phenol)), polycarboxylic acids (e.g. tribenzenetriacetic acid, hydroxybenzendicarboxylic acid, [(hydroxyphenylene)dixoy]diacetic acid, tris(carboxymethoxy)benzene, and triazine-tricarboxylic acid derivatives, such as (triazinetriyltroxy)triacetic acid and 1,3,5-triazine-2,4,6-tricarboxylic acid), and anionic polymers (cellulose sulfate, cellulose sulfate acetate, dextran sulfate, naphthalene sulfonate derivatives, polystyrene sulfonate, carrageenans, polycarboxylic acid, or polyvinylpyrrolidone, and where other polyanionic compounds are polyphosphorylated polymers, suramin, cyclodextrin sulfate, or multisulfated and multiphosphorylated peptides and alkyl chains).

In another aspect, the compounds of Formulas I-VIII display antiviral and/or antimicrobial activity.

In another aspect, the compounds of Formulas I-VIII display anti-HIV activity.

In one aspect, the compounds of Formulas I-VIII may be in the form of a composition which comprises a carrier, additive, or excipient.

In another aspect, the compounds of Formulas I-VIII may be in the form of a composition which may be used to treat or prevent infection, transmission, or acquisition of HIV/AIDS.

In another aspect, the compounds of Formulas I-VIII may be in the form of a composition that may be applied vaginally, anally, rectally and over the penis and other areas of the body to prevent sexual transmission of pathogens, in particular, that of HIV.

In another aspect, the compounds of Formulas I-VIII may be in the form of a composition that may be used as a microbicide to prevent or reduce sexual transmission of pathogens such as HIV, herpes simplex virus (HSV), human papilloma virus (HPV), *Chlamydia trachomatis* (CT), *Neisseria gonorrhoeae* (NG), *Haemophilus ducreyi* (HD) and others.

In another aspect, the compounds of Formulas I-VIII may be in the form of a composition that may be used as a contraceptive, especially for vaginal application.

In another aspect, the compounds of Formulas I-VIII may be in the form of a composition that may be used in a method for preventing or reducing sexual transmission of pathogens by delivering the composition of matter of formulas I-VII in solid or semi-solid forms, such as a tablet, gel, cream, ointment, pessary, or by virtue of a cervical/vaginal device such as a ring, cap, diaphragm or the like.

In another aspect, the compounds of Formulas I-VIII, or their parent nucleosides, may be chemically linked to another compound directly or through a linker, wherein the other compound is another nucleoside, a polymer, or a polyanionic molecule, wherein this compound is cellulose sulfate, cellulose sulfate acetate, dextran sulfate, naphthalene sulfonate derivatives, polystyrene sulfonate, carrageenans, polycarboxylic acid, polyvinylpyrrolidone, or cyclodextrin sulfate, and where other polyanionic compounds are polyphosphorylated polymers, suramin, or multisulfated and multiphosphorylated peptides and alkyl chains.

In another aspect, a multivalent scaffold may be used to attach one or more of the compounds of Formulas I-VIII, or its parent nucleoside, wherein the scaffold may be a derivative containing one to three 2-hydroxybenzyl alcohol (e.g., 4,4'-dihydroxy-3,3'-di-(hydroxymethyl)diphenylmethane, 4,6-dihydroxy-1,3-benzenedimethanol, 4,4',4''-methanetriyltris(2-(hydroxymethyl)phenol)), polycarboxylic acids (e.g. tribenzenetriacetic acid, hydroxybenzendicarboxylic acid, [(hydroxyphenylene)dixoy]diacetic acid, tris(carboxymethoxy)benzene, and triazine-tricarboxylic acid derivatives, such as (triazinetriyltroxy)triacetic acid and 1,3,5-triazine-2,4,6-tricarboxylic acid), and anionic polymers (cellulose sulfate, cellulose sulfate acetate, dextran sulfate, naphthalene sulfonate derivatives, polystyrene sulfonate, carrageenans, polycarboxylic acid, or polyvinylpyrrolidone, and where other polyanionic compounds are polyphosphorylated polymers, suramin, cyclodextrin sulfate, or multisulfated and multiphosphorylated peptides and alkyl chains).

In another aspect, the compounds of Formulas I-VIII, or their parent nucleosides, may be chemically linked to another compound, wherein the other compound displays anti-HIV properties, wherein the anti-HIV agent is cellulose sulfate, cellulose sulfate acetate, cellulose acetate, suramin, dendrimers, cyclodextrins, or another reverse transcriptase inhibitor (RTI). In a further embodiment, the RTI may be a nucleoside (eg, AZT, FLT, 3TC, 4dT, FTC, ddC), nucleotide (eg, tenofovir), non-nucleoside (eg, efavirenz, nevirapine, delavirdine, dapivirine, UC-781, MIV-150) or one of its analogues.

In another aspect, the compounds of Formulas I-VIII or one or more nucleoside or nucleotide analogs may be linked to a scaffold directly or through a linker in the presence or absence of fatty acids or fatty alcohols.

In another aspect, the compounds of Formulas I-VIII, or their parent nucleosides, may be chemically linked to another compound to provide a composition of matter and may contain a carrier or excipient. In another aspect, the composition of matter may be used to treat or prevent infection or transmission of HIV/AIDS and may be applied vaginally, anally, rectally and over the penis and other areas of the body to prevent sexual transmission of pathogens, in particular, that of HIV. In another aspect, the composition of matter may be used as a microbicide to prevent or reduce sexual transmission of pathogens such as HIV, HSV, HPV, CT, NG, HD and others. In another aspect, the composition of matter may be used as a contraceptive, especially for vaginal application.

In another aspect, the compounds of Formulas I-VIII, or their parent nucleosides, may be chemically linked to another compound to provide a composition of matter and may contain a carrier or excipient, and may be used in a method for treating, preventing, or reducing sexual transmission of pathogens by delivering the composition of matter in solid or semi-solid forms, such as a tablet, film, gel, cream, ointment, pessary or by virtue of a cervical/vaginal device such as a ring, cap, diaphragm, or the like.

In another aspect, the compounds of Formulas I-VIII, or their parent nucleosides, may be chemically linked to another compound to provide a composition of matter and may contain a carrier or excipient, and may be used in a method for preventing conception and pregnancy by delivering any of the compositions of matter disclosed above intravaginally in the form of a solid or semi-solid or by virtue of a device such as a ring, cap, diaphragm or the like.

In another aspect, the compounds of Formulas I-VIII, or their parent nucleosides, may be chemically linked to another compound to provide a composition of matter and may contain a carrier or excipient, and may be used in a method for preventing or treating HIV infection as part of a combination product, wherein the other components of the product are other nucleoside, nucleotide, and non-nucleoside RTIs, or protease inhibitors, or integrase inhibitors or entry/fusion inhibitors, or other HIV inhibitors known to those skilled in the art.

BRIEF DESCRIPTION OF THE FIGURES

FIG. 1 shows the general format of conjugation between nucleosides, linker, fatty acids or fatty alcohols, and scaffolds.

FIG. 2 displays general chemical structures of some of the nucleoside-fatty acid, nucleoside-fatty alcohol, multivalent scaffold-nucleoside conjugates.

FIG. 3A shows the general chemical structures of the claimed compounds (Formulas I-VI).

FIG. 3B shows the general chemical structures of the claimed compounds (Formula VII).

FIG. 3C shows the general chemical structures of the claimed compounds (Formula VIII).

FIGS. 27-28 show the synthesis of cycloSaligenyl derivatives containing two nucleotides.

DETAILED DESCRIPTION OF THE INVENTION

Figure 4:
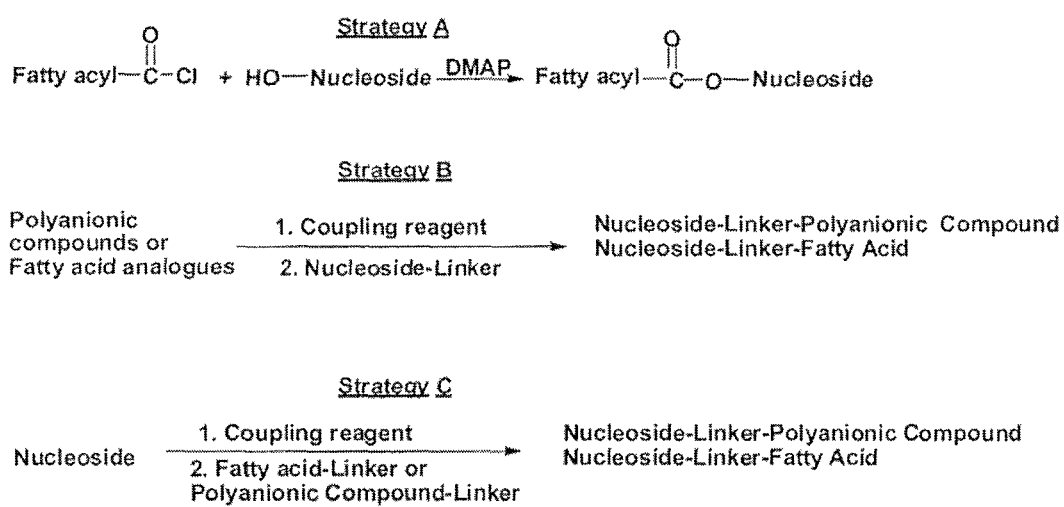
FIG. 4 depicts the general strategies for the synthesis of nucleoside-fatty acid conjugates and nucleoside-polyanionic analogue conjugates.

For the purposes of promoting an understanding of the principles of the invention, reference will now be made to preferred embodiments and specific language will be used to describe the same. It will nevertheless be understood that no limitation of the scope of the invention is thereby intended, such alteration and further modifications of the invention, and such further applications of the principles of the invention as illustrated herein, being contemplated as would normally occur to one skilled in the art to which the invention relates.

The term "alkyl" as used herein denotes an unbranched or branched chain hydrocarbon residue containing 1 to 18 carbon atoms. The term "aryl" as used herein denotes an optionally substituted monocyclic or polycyclic-aromatic group comprising carbon and hydrogen atoms. Examples of suitable aryl groups include, but are not limited to, phenyl and naphthyl (e.g. 1-naphthyl or 2-naphthyl). The term "amino acid" as used herein refers to naturally occurring .alpha. amino carboxylic acids, as well as to optical isomers (enantiomers and diastereomers), synthetic analogs and derivatives thereof. The term "protecting group" as used herein means a chemical group that (a) preserves a reactive group from participating in an undesirable chemical reaction; and (b) can be easily removed after protection of the reactive group is no longer required.

A "nucleoside" contains a heterocyclic nitrogenous base, either adenine (A), guanine (G), cytosine (C), or uracil (U) joined to a ribose or deoxyribose. As used herein, a "nucleoside" includes a naturally occurring or synthetic nucleoside, nucleoside analog, or nucleoside derivative thereof. A "nucleoside analog" as used herein includes an analog of ribonucleosides and deoxyribonucleosides and the triphosphates thereof. For instance, structural groups are optionally added to the sugar or base of a nucleoside, such as a methyl or allyl group at the 2'-0 position on the sugar, or a fluoro group which substitutes for the 2'-0 group, or a bromo group on the nucleoside base. A "nucleoside derivative" as used herein includes a nucleoside or a nucleoside analog attached to a phosphate group as phosphomonoester, phosphodiester, phosphotriester, cyclic phosphotriester, cyclic phosphite triester, or phosphoramidate triester.

By "complex" is meant a compound which is made up structurally of two or more compounds or ions, that is, a compound formed by a combination of substances that are themselves capable of independent existence. In an aspect, "complex" describes the chemical moiety produced by the interaction of two or more of the substituents disclosed herein.

Scaffolds are defined as skeleton, core, or template of the structure that multiple functional groups and moieties are attached. The scaffolds may have multiple positions for multivalent linkages. The scaffolds may be polymers or smaller molecules containing several functional groups (e.g., hydroxyl, amino, or carboxylic acid groups) for attaching to other compounds. Scaffolds may be directly or indirectly attached through linkers to active components of the conjugates, such as nucleosides or nucleoside derivatives. Scaffolds are able to attach more than two molecules directly or indirectly through linkers or spacers.

Linkers or spacers are flexible or rigid moieties used to attach the scaffolds to the active components of the conjugates, such as nucleosides or nucleoside derivatives, or to connect directly two or more active components, such as several nucleosides or nucleoside derivatives.

This invention provides novel fatty acid or fatty alcohol substituted nucleoside derivatives and nucleoside multivalent scaffold (e.g., polyanionic polymers, peptides, polycarboxylic acids, polycycloSaligeny groups) conjugates displaying potent anti-HIV activity. These agents may be used systemically for the treatment or prevention of HIV/AIDS. They may also be used as topical microbicides to prevent acquisition of HIV infection through skin and mucosa. The invention provides compounds that are ideal candidates for this application preventing the acquisition of sexually transmitted disease.

The present invention provides methods of synthesis, compositions of matter and applications of newly discovered substituted nucleoside and nucleoside-multivalent scaffolds conjugates.

The fatty acid, fatty alcohol, peptides, polycarboxylic acids, phosphodiesters, and polyanionic conjugates of nucleoside analogues are based on the general Formula I-VIII (FIGS. 3A-C), wherein one or more of 3'-deoxynucleosides are attached directly or indirectly through a linker to long chain fatty acids, long chain fatty alcohols, peptides, polycarboxylic acids, polyanionic molecules (e.g., polysulfated carbohydrates), or both at 5'-position of the carbohydrate moiety and/or N4 position of base moiety of nucleoside analogues.

The nucleoside analogues are based on the general Formula I-VIII, wherein nucleoside analogues are pyrimidine derivatives based on the structures of 3'-deoxythymidine, 3'-deoxyuridine, 3'-deoxycytidine, 3'-thiacytidine, their stereoisomers, their modified forms with substitutions at positions 5, 6, and substitutions at positions 1', 2', 3', 4', and 5' of carbohydrate moiety, purine nucleosides based on the structures of 3'-deoxyguanidine, 3'-deoxyadenosine, their modified forms with substitutions at positions 2, 4, 6, 8, and/or N4 of base moiety, substitutions at positions 1', 2', 3', 4', and 5' of carbohydrate moiety, and/or double bond between C3' and C4' in carbohydrate moiety (FIG. 3).

In one aspect, the invention provides methods of synthesis for the above-mentioned analogues using conjugation strategies which employ appropriate coupling reagents and linkers (Agarwal et al., 1990; Parang et al., 1998; Torrence et al., 1993; Palomino et al., 1989; Chu et al, 1990; Seki et al., 1990; Gao et al., 1999; Vlieghe et al., 2002). These methods include acylation of appropriately protected nucleosides with fatty acyl chloride in the presence of 4-(dimethylamino)pyridine (DMAP). In another strategy, appropriate bifunctional linkers are conjugated first with appropriately protected nucleosides, followed by second coupling reaction with fatty acids analogues or polyanionic compounds. In another strategy, appropriate bifunctional linkers are first conjugated with fatty acids or polyanionic compounds, followed by second coupling reaction with appropriately protected nucleosides (FIG. 4). When required nucleosides are protected with appropriate protecting groups, such as DMTr for protection of amino groups or tert-butyldimethylsilyl (TBDMS) for protection of hydroxyl groups.

Figure 5:
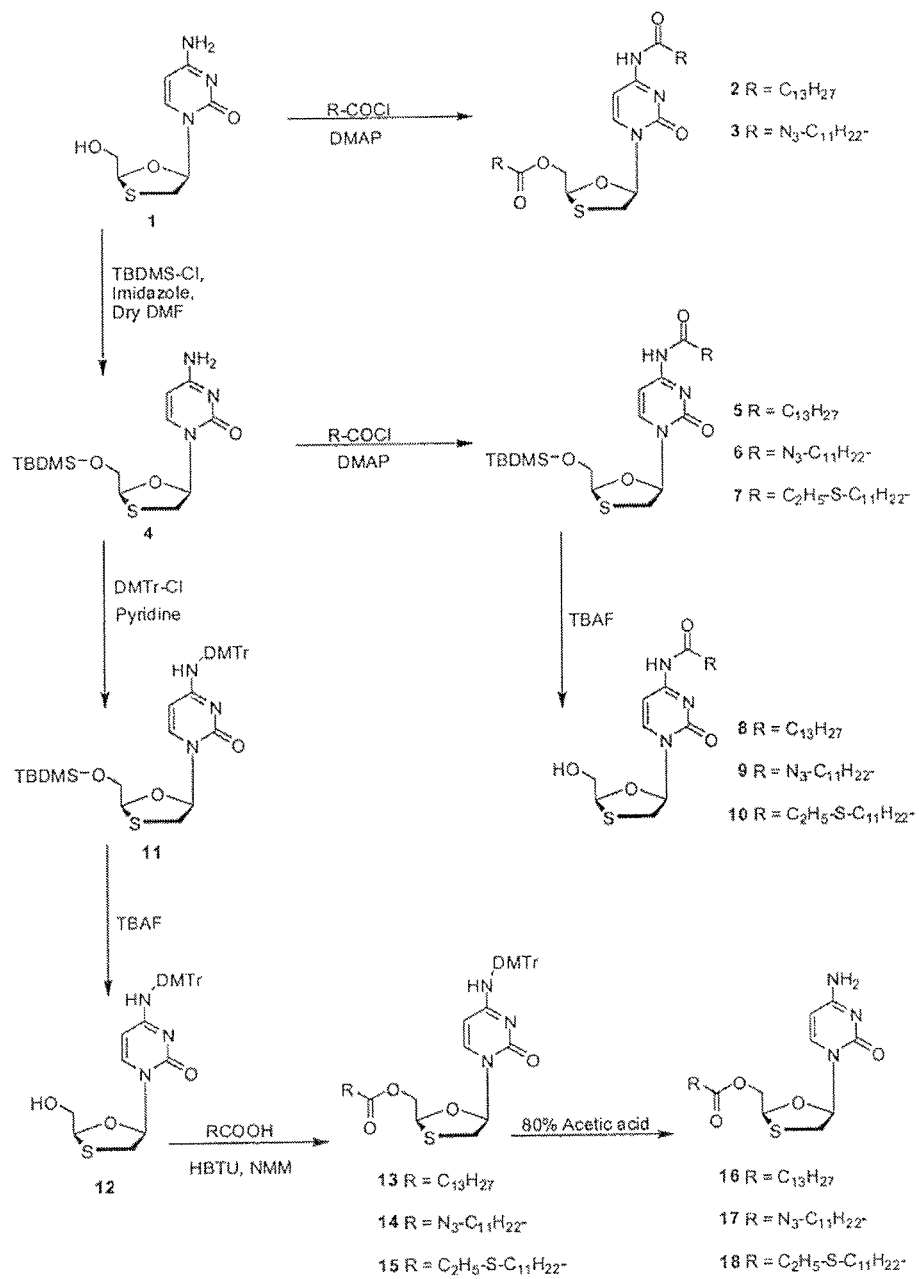
FIG. 5 depicts the synthesis of lamivudine derivatives.

For example, for the synthesis of fatty acyl substituted analogues of lamivudine, 5'-hydroxyl group was first protected with TBDMS in the presence of tert-butyldimethylsilyl chloride (TBDMS-Cl), imidazole in dry DMF to afford 5'-t-butyldimethylsilyl lamivudine. N4 substituted analogues were synthesized by acylation in the presence of fatty acyl chloride and DMAP in dry benzene, followed by deprotection of TBDMS group with tert-butylammonium fluoride (TBAF). For the synthesis of 5'-O-fatty acyl derivatives of lamivudine after initial protection of 5'-OH of lamivudine with TBDMS, the protection of N4-amino group of 5'-protected lamivudine was carried out in the presence of DMTr-Cl in dry pyridine to afford N-DMTr-5'-t-butyldimethylsilyl lamivudine. The deprotection of TBDMS in the presence of TBAF, followed by esterification of 5'-hydroxyl group in the presence of fatty acids, HBTU and N-methylmorpholine (NMM) afforded 5'-0-fatty acyl-N-4-DMTr derivative of lamivudine. The final deprotection of DMTr was accomplished with acetic acid to afford 5'-O-fatty acyl derivatives of lamivudine. Disubstituted derivatives of lamivudine were synthesized by the reaction of lamivudine with fatty acyl chlorides in anhydrous benzene in the presence of DMAP (FIG. 5). A similar strategy was used for the synthesis of '-substituted analogues of emtricitabine. 5'-Substituted analogues of stavudine, AZT, and FLT were synthesized by the reaction of the nucleosides with prepared fatty acyl chlorides in dry benzene in the presence of DMAP.

In another aspect, these analogues are fatty acid derivatives, fatty alcohol derivatives, or polyanionic derivatives of 3'-azido-3'-deoxythymidine (zidovudine, AZT), 3'-fluoro-3'-deoxythymidine, 2',3'-dideoxy-3'-thiacytidine (lamivudine, 3TC), 2',3'-didehydro-2'3'-dideoxythymidine (stavudine, 4dT), 2',3'-dideoxycytidine (zalcitabine, ddC), and (−)-β-2',3-dideoxy-5-fluoro-3'-thiacytidine (emtricitabine, FTC). However, those skilled in the art will recognize that these fatty acid analogues may be derivatized from any suitable nucleoside conjugated with these fatty acid or polyanionic analogues.

Figure 6:
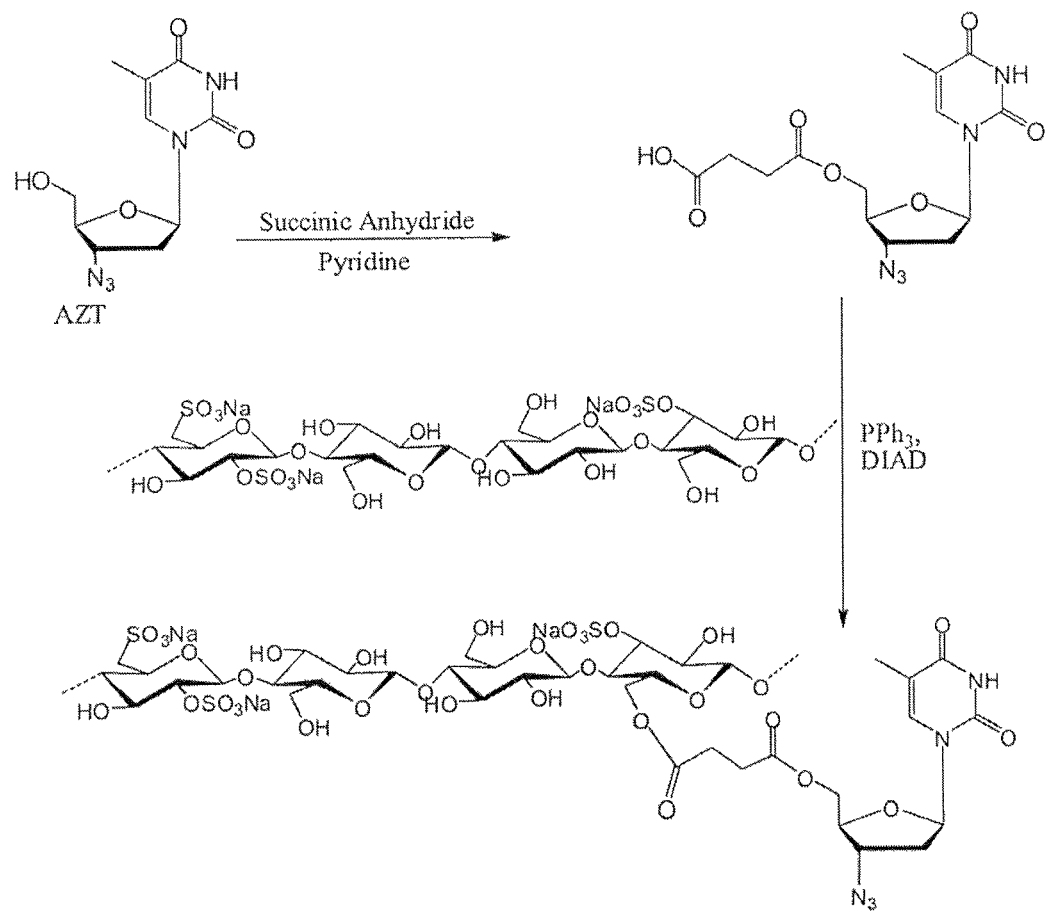
FIG. 6 depicts the synthesis of an AZT-succinate-sodium cellulose sulfate conjugate.
Figure 7:
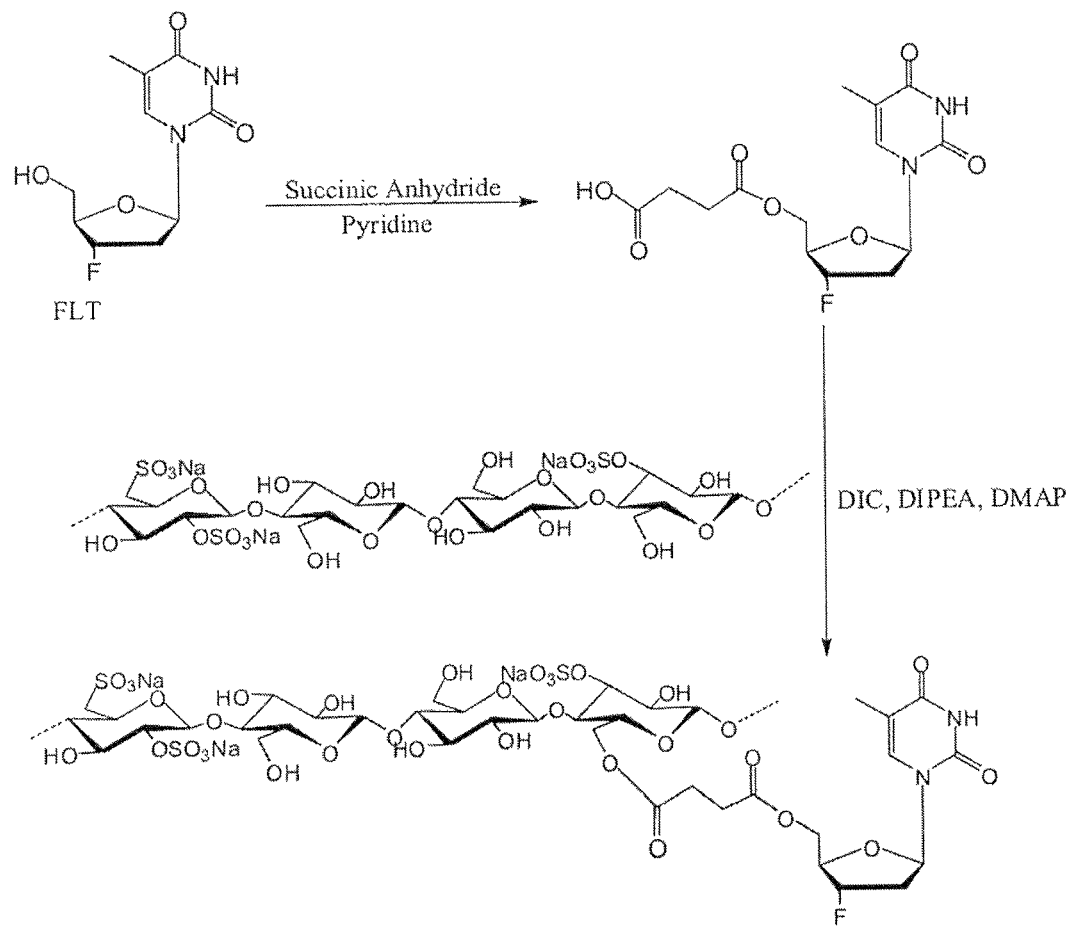
FIG. 7 depicts the synthesis of a FLT-succinate-sodium cellulose sulfate conjugate.
Figure 8:
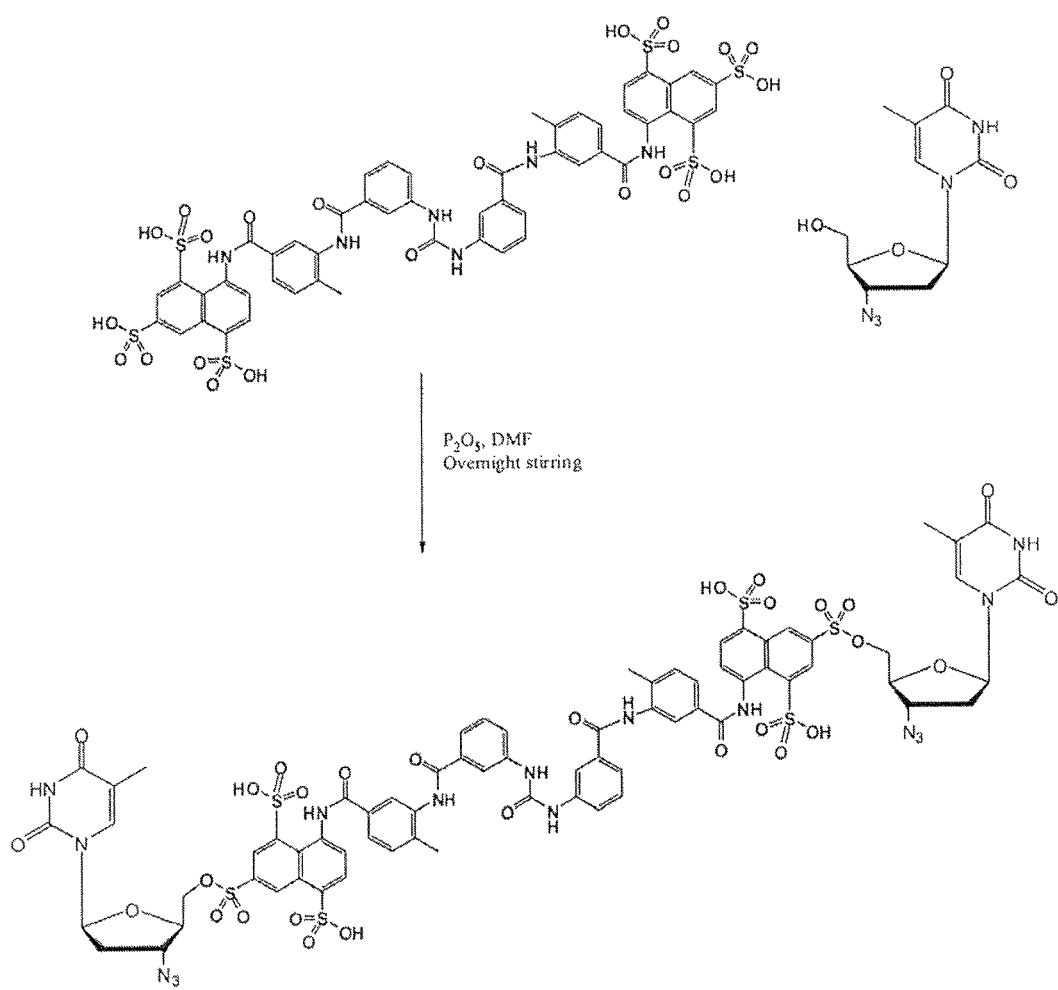
FIG. 8 depicts the synthesis of an AZT-suramin conjugate.

It is a further object of this invention to describe the synthesis of polyanionic derivative of nucleosides and biological activity of the nucleoside derivatives, chemically conjugated or linked, directly or indirectly, to other compounds such as cellulose sulfate and suramin (FIGS. 6-8). In one strategy, appropriate bifunctional linkers are conjugated first with appropriately protected nucleosides, followed by a second coupling reaction with polyanionic compounds.

For example, AZT-succinic acid conjugate was reacted with sodium cellulose sulfate in the presence of PPh$_3$ and DIAD to produce AZT-succinic-sodium cellulose sulfate conjugate (FIG. 6). Similarly, FLT-succinic acid was reacted with sodium cellulose sulfate in the presence of DIC, DMAP, and DIPEA (FIG. 7). Suramin was reacted directly with AZT and FLT in the presence of P$_2$O$_5$ in DMF to afford suramin-AZT and suramin-FLT conjugates, respectively (FIG. 8).

In another strategy, appropriate bifunctional linkers are first conjugated with polyanionic compounds, followed by second coupling reaction with appropriately protected nucleosides.

Figure 9:
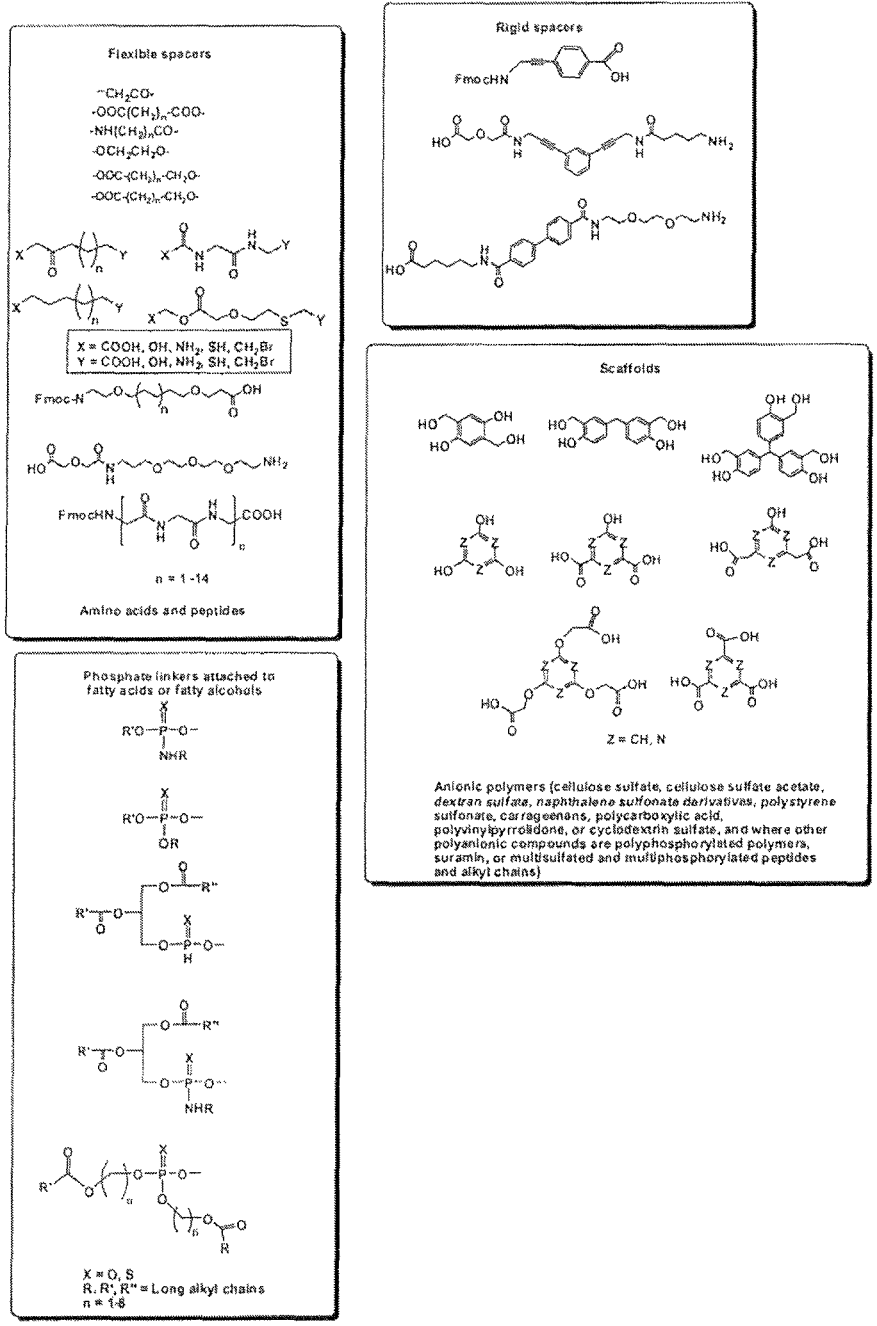
FIG. 9 depicts the flexible and rigid linkers for the synthesis of conjugates of nucleoside-polyanionic derivatives.

Linkers are known to those skilled in the art. The flexible or rigid linkers may be alkyl and/or aryl chains with different lengths, phosphoglycerate, phosphoramidate, phosphomonoester, phosphodiester, phosphotriester, triglycerides, cyclic phosphotriesters, cyclic phosphite triesters, 2-hydroxybenzyl alcohol, cycloSaligenyl groups, acetate, dicarboxylic acid esters (—OOC—(CH$_2$)$_n$—COO—, n=0-14 such as succinate), L or D-amino acyl (—NH—(CHR)$_n$—CO—, R=H or side chains of amino acids, n=1-25 such as γ-aminobutyric acid, glutamic acid, aspartic acid, serine, threonine forming linear or cyclic peptides), polyethers (e.g., ethylene glycol ethers (—OCH$_2$CH$_2$O)$_n$—, n=1-14), carboxylic acid esters ethers (—OOC—(CH$_2$)$_n$—CH$_2$O—, n=0-14), polyamides, or any combination of the linkers (e.g., —OOC(CH$_2$)$_n$CONH(CH$_2$CH$_2$O)$_n$NHCO(CH$_2$)$_n$COO—). Exemplary linkers are shown in FIG. 9.

Scaffolds are known to those skilled in the art. The scaffolds may be derivatives containing one to three 2-hydroxybenzyl alcohol (e.g., 4,4'-dihydroxy-3,3'-di-(hydroxymethyl)diphenylmethane, 4,6-dihydroxy-1,3-benzenedimethanol, 4,4',4"-methanetriyltris(2-(hydroxymethyl) phenol)), polycarboxylic acids (e.g. tribenzenetriacetic acid, hydroxybenzenecarboxylic acid, [(hydroxyphenylene) dioxy]diacetic acid, tris(carboxymethoxy)benzene, and triazine-tricarboxylic acid derivatives, such as (triazinetriyltroxy)triacetic acid and 1,3,5-triazine-2,4,6-tricarboxylic acid), and anionic polymers (cellulose sulfate, cellulose sulfate acetate, dextran sulfate, naphthalene sulfonate derivatives, polystyrene sulfonate, carrageenans, polycarboxylic acid, polyvinylpyrrolidone, or cyclodextrin sulfate, and where other polyanionic compounds are polyphosphorylated polymers, suramin, or multisulfated and multiphosphorylated peptides and alkyl chains). Exemplary scaffolds are shown in FIG. 9.

In contact with cells, the linkers are cleaved and the two components are separated. In the case of large anionic polymers such as cellulose sulfate, this compound remains outside the cells inhibiting HTV cell entry, while the nucleoside derivative is rapidly taken up, inhibiting HIV reverse transcriptase and replication.

In one aspect, this invention provides examples of antiviral activity of some of the fatty acid analogues against HIV-1, cell-free and cell-associated, X4 and R5 variants (Table 1). Some of the discovered analogues exhibit higher antiviral activity than their parent nucleosides.

Figure 10:
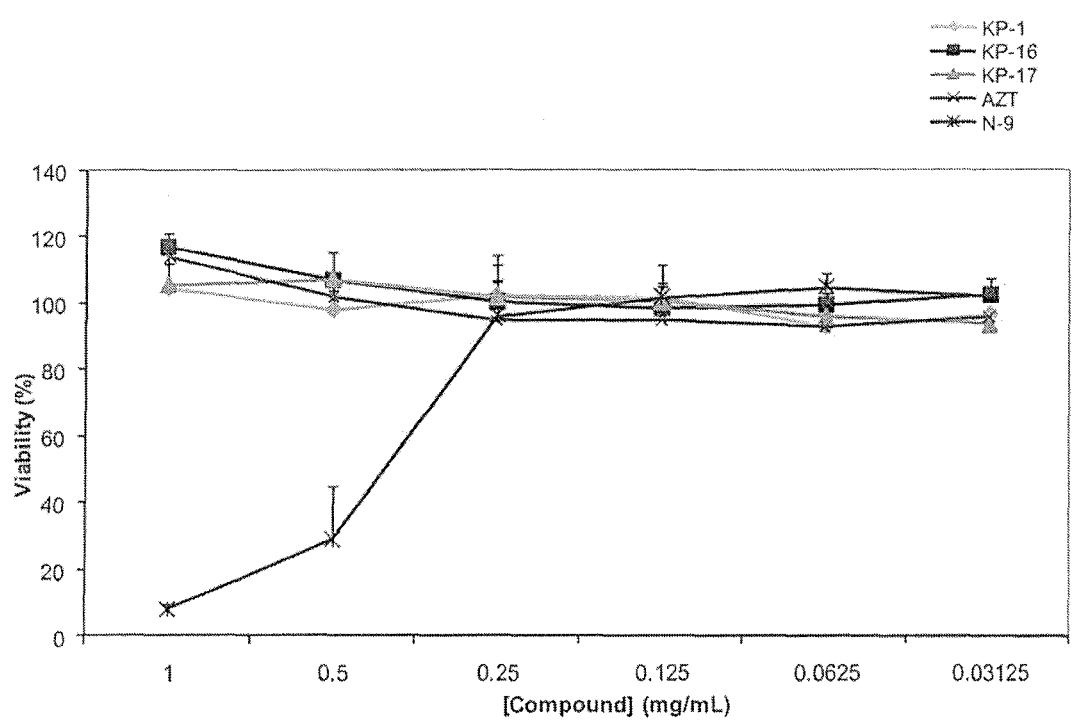
FIG. 10 shows vaginal cell toxicity of fatty acid derivatives of FLT.
Figure 11:
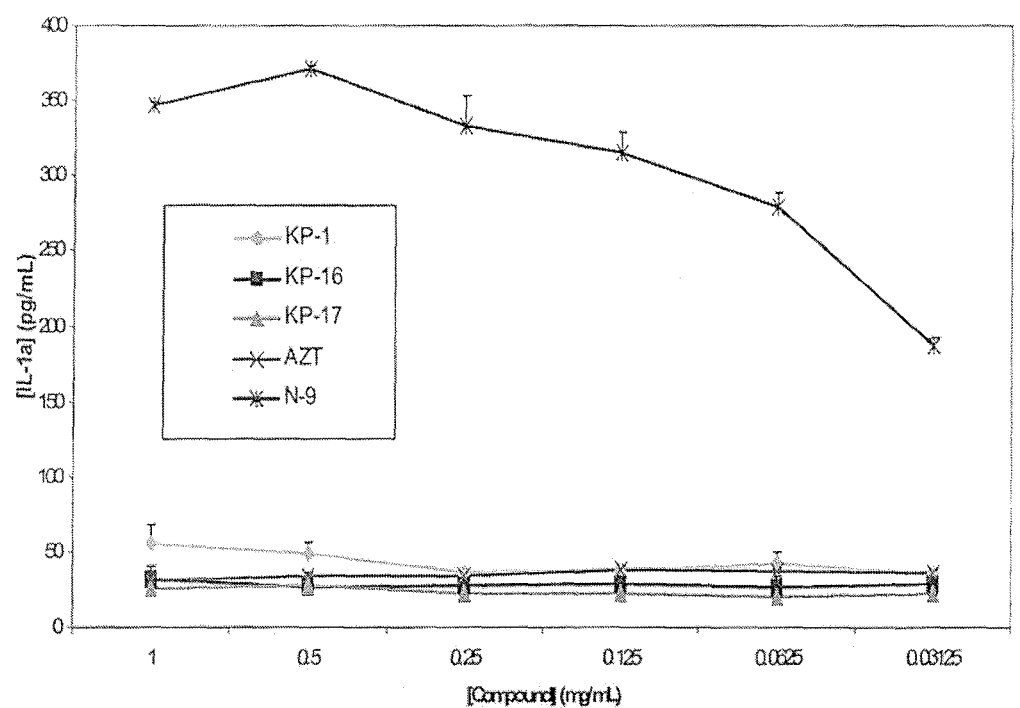
FIG. 11 shows IL-1 alpha production by human vaginal cells incubated with fatty acid derivatives of FLT.

Most of the derivatives are more potent than AZT. 2',3'-Dideoxy-5-fluoro-3'-thiacytidine derivatives are the most potent compounds and their activities were significantly higher than physical mixtures of the corresponding compounds. Furthermore, 3'-fluoro-2',3'-dideoxythymidine derivatives are also potent and show no signs of cytotoxicity against Hela cells, peripheral blood mononuclear cells and human vaginal cells (FIGS. 10 and 11). Unlike AZT, they did not show a drop in potency against multidrug resistant virus (Table 2) and are highly active against cell-associated virus. In general, fatty ester conjugates of FLT performed much better against cell-associated HIV compared to the corresponding physical mixtures.

Figure 12:
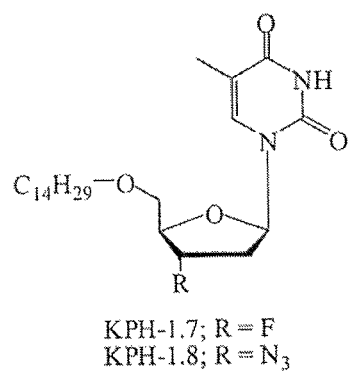
FIG. 12 displays the chemical structures of tetradecanol ether derivatives of FLT and AZT.

Ether derivatives of FLT and AZT substituted with 5'-tetradecanol (FIG. 12) were significantly less potent than the corresponding ester derivatives (Table 1). These data demonstrate that the ester bonds are important in enabling anti-HIV activity. The ester needs to be hydrolyzed rendering parent nucleosides and fatty acids for the compound to display antiviral activity. In ether derivatives, the hydrolysis is not possible because the ether bond is not susceptible to the cleavage action of esterases.

Unexpectedly, FLT derivatives were found to inhibit growth and multiplication of *H. ducreyi*, a bacterium known to cause chancroid and be a risk factor for acquisition of HIV infection (Table 3). Certain fatty acid substituted nucleoside derivatives display anti-microbial activity against sexually transmitted pathogens other than HIV.

Figure 13:
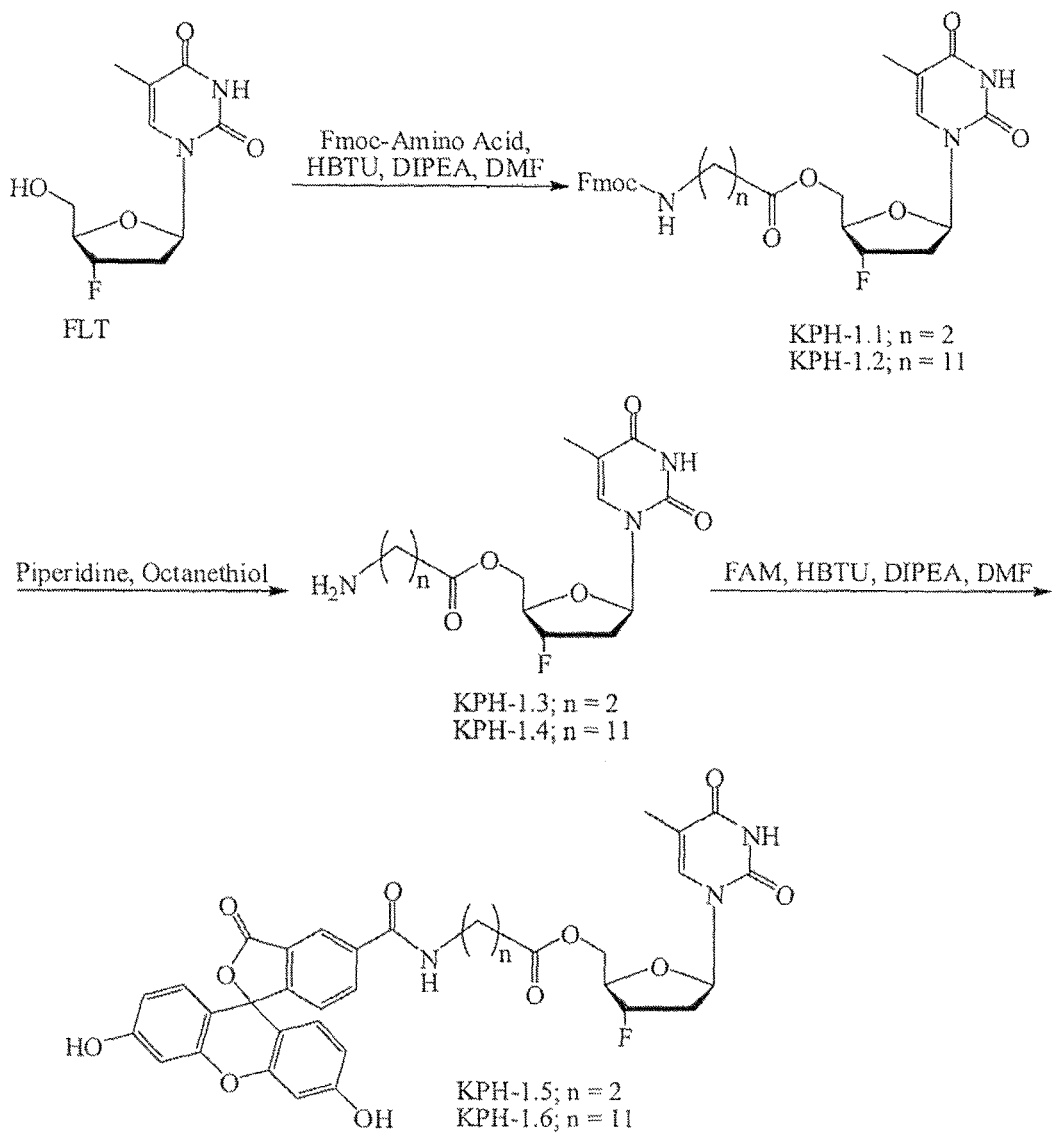
FIG. 13 depicts the synthesis of 5'-carboxyfluorescein derivatives of FLT through different linkers

In another aspect, this invention provides the synthesis and evaluation of 5(6)-carboxyfluorescein (FAM) derivatives of nucleosides. For example, FLT was attached to 5(6)-carboxyfluorescein using β-alanine and 12-aminododecanoic acid as linkers. First, FLT was reacted with the corresponding Fmoc-amino acid in presence of HBTU and DIPEA. Second, N-Fmoc deprotection to free amino group was achieved in the presence of piperidine. Finally, FAM was attached to free amino group in the presence of HBTU and DIPEA to afford 5(6)-carboxyfluorescein derivatives of FLT, KPH-1.5 and KPH-1.6 (FIG. 13). Similarly, FAM derivatives of 3TC were synthesized. These compounds were used for cellular uptake studies to determine cellular uptake profile of fatty acyl ester derivatives of FLT, 3TC, and other nucleosides. FLT attached to FAM through β-Alanine (KPH-1.5) was used as a control FLT analogue. FLT attached to FAM through 12-aminododecanoic acid (KPH-1.6) was used as an analogue of 3'-fluoro-2',3'-dideoxy-5'-O-(12-azidododecanoyl)thymidine (KP-1) and other fatty acid ester analogues of FLT. 3'-Fluoro-2',3'-dideoxy-5'-O-(12-aminododecanoyl)thymidine and showed anti-HIV activities comparable to other fatty acyl derivatives of FLT. KPH-1.6 (3'-fluoro-2',3'-dideoxy-5'-O-(12-(N-5(6)carboxylfluoresceinaminododecanoyl)thymidine) showed slightly lower anti-HIV activity when compared with unsubstituted 12-aminododecanoyl derivative (Table 1).

The human T lymphoblastoid cells CCRF-CEM (ATCC no. CCL-119) were used for the study and were grown to the 70% confluency in the culture media. Cells were incubated with the fluorescein-substituted conjugates (KPH-1.5 and KPH-1.6) in different time periods, concentrations and in the presence or absence of with trypsin, DMSO and FAM were used as control for the study. The cells were analyzed by flow cytometry (FACSCalibur: Becton Dickinson) using FITC channel and CellQuest software. The data presented are based on the mean fluorescence signal for 10000 cells collected. All the assays were carried out in triplicate.

Figure 14:
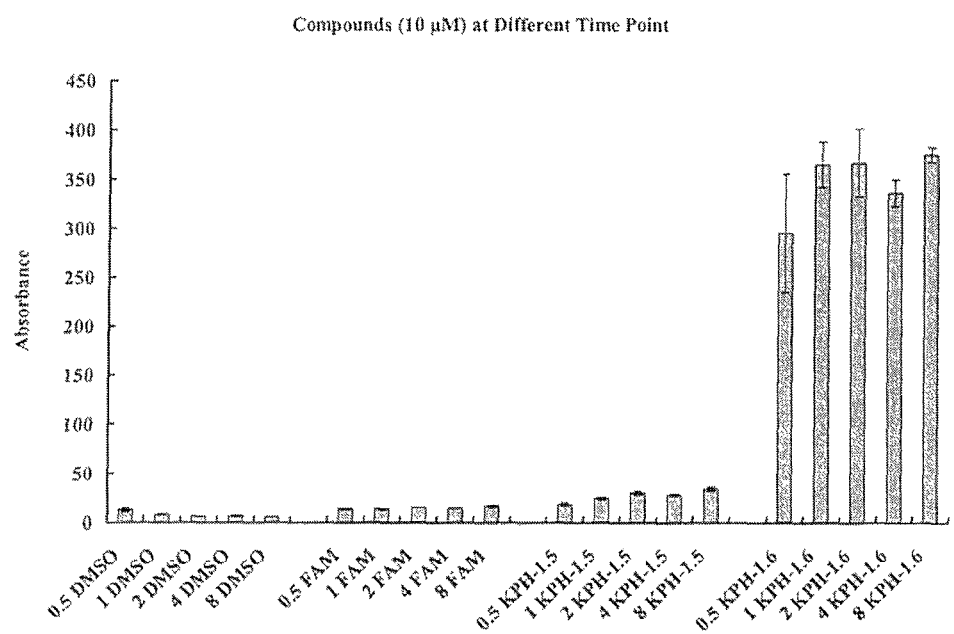
FIG. 14 shows the cellular uptake studies for 5(6)-carboxyfluorescein derivatives of FLT along with FAM and DMSO as controls at different time intervals.

Cells were incubated with 10 µM of the compounds in different time periods (0.5 h, 1 h, 2 h, 4 h and 8 h, FIG. 14). KPH-1.6 exhibited 10-15 fold higher cellular uptake than that of KPH-1.5 and FAM alone. The results clearly indicate that presence of long chain enhances the cellular uptake of FLT, by increasing lipophilicity. The continuous incubation of cells with compounds up to 8 h did not show significant difference in the cellular uptake, suggesting that most of the fatty acyl ester derivative is absorbed into cells in the first 30 minutes and the cellular uptake was not time dependent.

Figure 15:
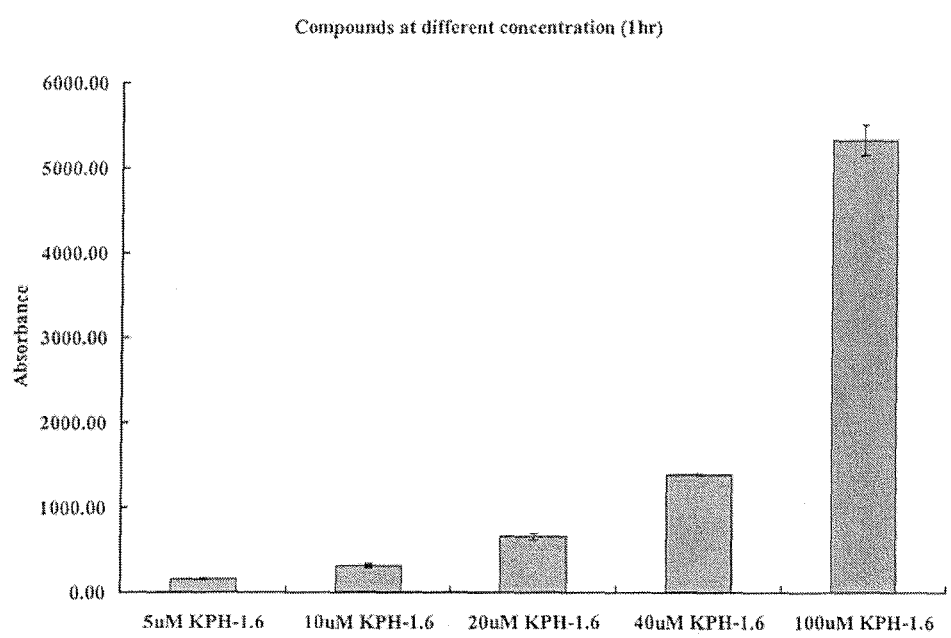
FIG. 15 demonstrates the cellular uptake studies for 5(6)-carboxyfluorescein derivatives of FLT along with FAM and DMSO as controls at different concentrations.

Cells were also incubated with different concentrations (5, 10, 20, 40 and 100 µM) of carboxyfluorescein derivatives of FLT, KPH-1.5 and KPH-1.6 for 1 h (FIG. 15), and data suggest that the cellular uptake is concentration dependent.

Figure 16:
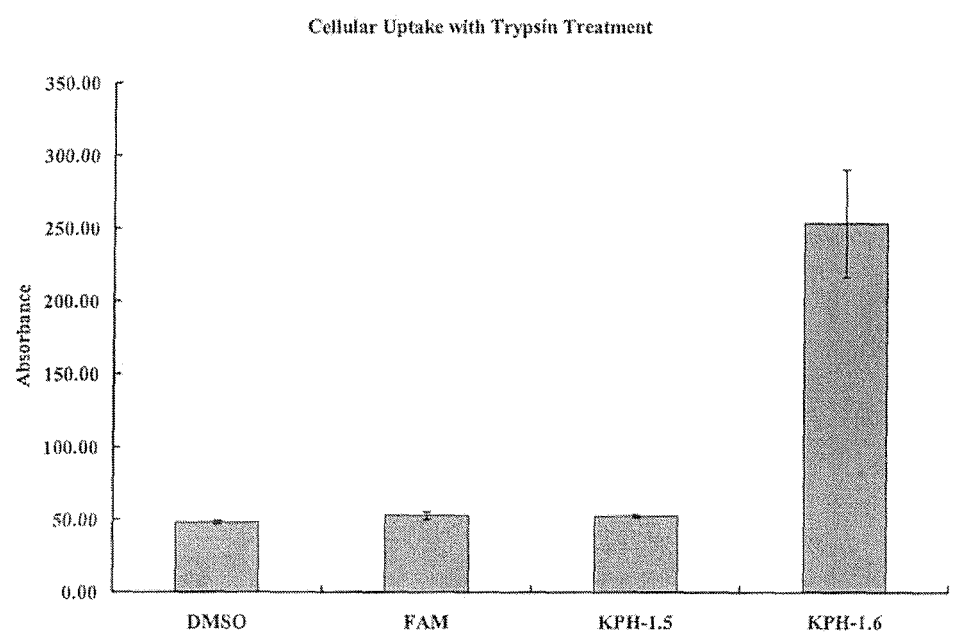
FIG. 16 shows the cellular uptake studies for 5(6)-carboxyfluorescein derivatives of FLT along with FAM and DMSO as controls after treatment with trypsin.

To confirm that the enhanced uptake of 5(6)-carboxyfluorescein derivatives of FLT, KPH-1.6, is not due to the absorption on the cell membrane surface, cells were incubated with 10 µM of DMSO, FAM, KPH-1.5 and KPH-1.6 for 1 h and then finally treated with trypsin for 5 min to wash the adsorbed molecules (if any) from the cell membrane. The cellular uptake studies after trypsin treatment showed that the cellular uptake of KPH-1.6 was still much higher than those of control compounds, FAM and KPH-1.5 (FIG. 16), suggesting that the higher cellular uptake of KPH-1.6 is not due to absorption to the cell membrane.

Figure 17A:
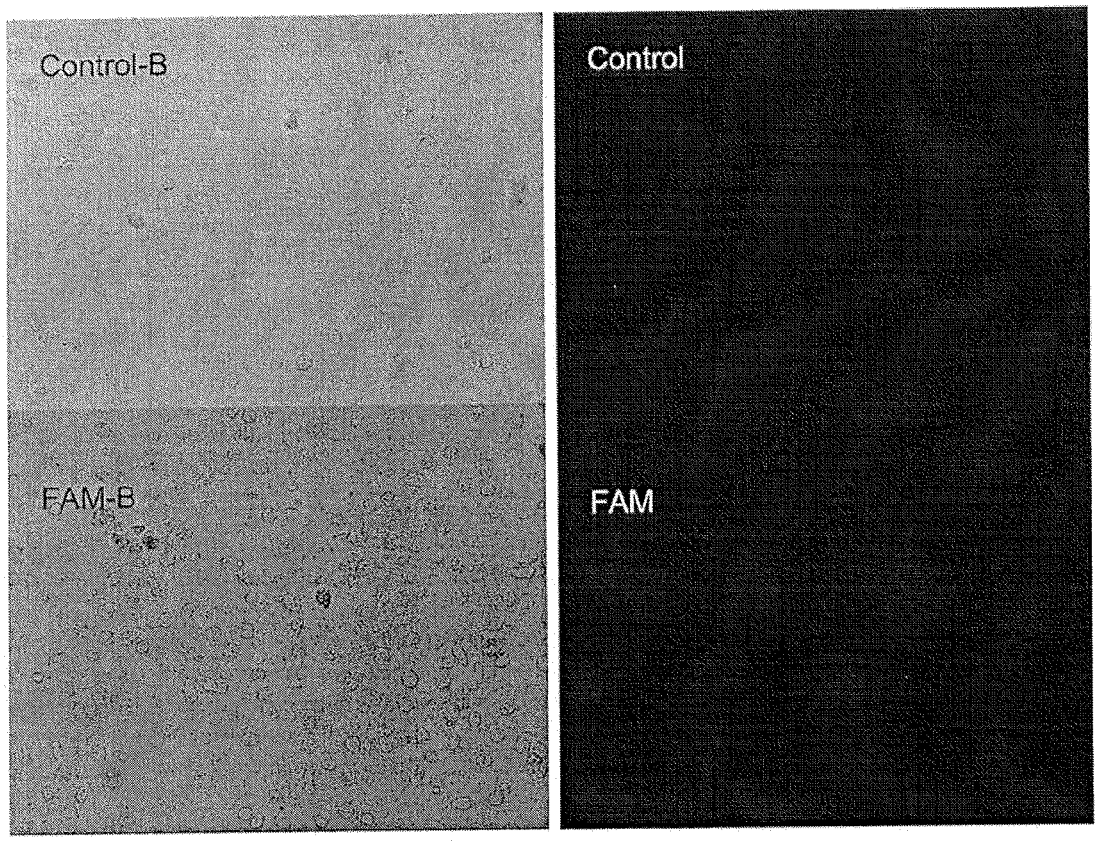
FIG. 17A shows real time fluorescence microscopy in live CCRF-CEM cell line. C=Control, FAM=5(6)-carboxyfluorescein.
Figure 17B:
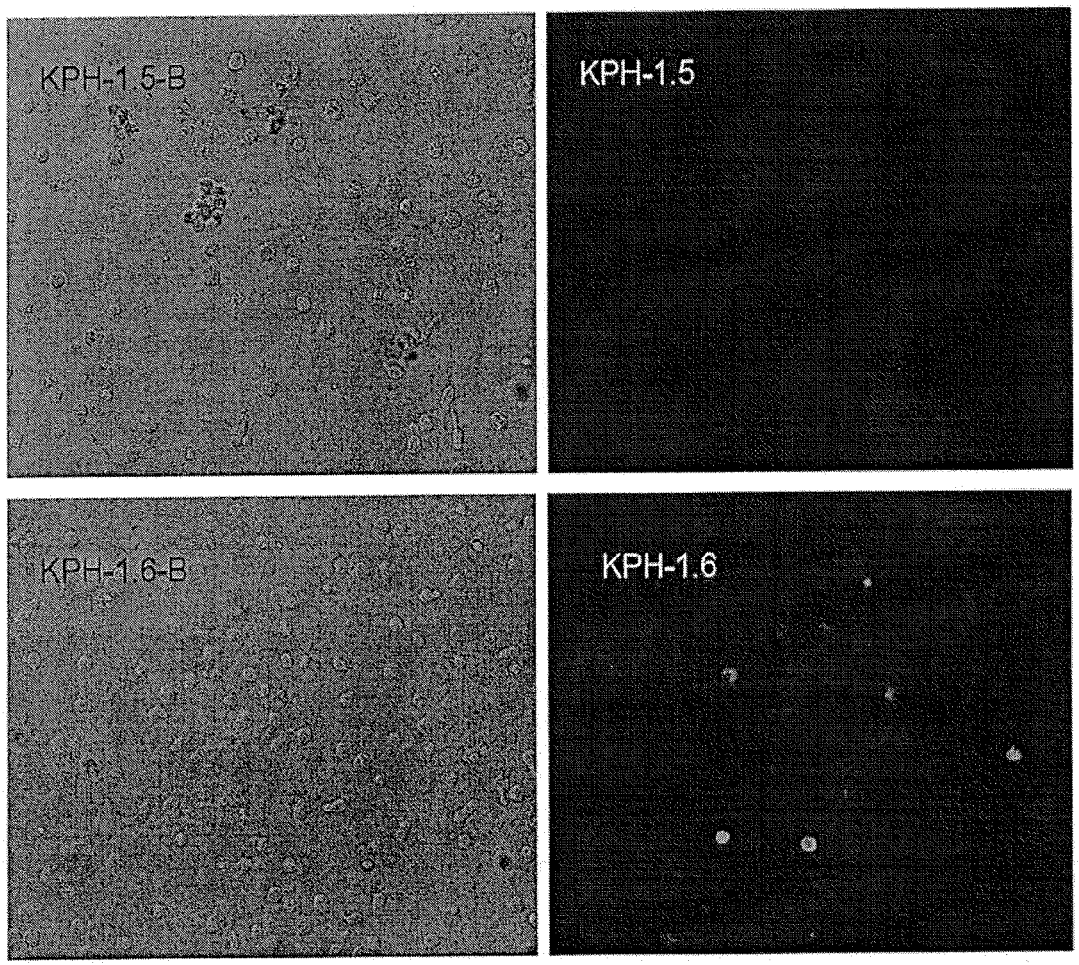
FIG. 17B shows real time fluorescence microscopy in live CCRF-CEM cell line incubated with 5(6)-carboxyfluorescein derivatives of FLT, KPH-1.5 and KPH-1.6.

Cells were incubated with 10 µM of DMSO, FAM, KPH-1.5 and KPH-1.6 for 1 h and then imaged using a light microscope (ZEISS Axioplan 2) equipped with transmitted light microscopy with a differential-interference contrast method and an Achroplan 40× objective. Cells showed no significant fluorescence when incubated with DMSO, FAM, and KPH-1.5 (FIG. 17). On the other hand, cells incubated with KPH-1.6 showed fluorescence. The results further confirm the higher cellular uptake of KPH-1.6, a fatty acyl derivative of FLT, in comparison to KPH-1.5 and FAM alone. Similar results were also observed with fluorescein-substituted derivative of 3TC. These data indicate that the fatty acyl derivatives of nucleosides have better cellular uptake than their parent nucleosides.

Polyanionic conjugates exhibit multiple mechanisms of action, which result in synergistic or additive activity. For example, a CS-AZT conjugate (acetate linker; 1.73% loading) was more effective than CS, especially against the R5 HIV-1 lab-adapted strain BaL. Sodium cellulose sulfate-acetate exhibited significantly higher potency than sodium cellulose sulfate against cell-free virus. Sodium cellulose sulfate-acetate conjugated with AZT (1.73%) and the physical mixture of sodium cellulose sulfate-acetate with AZT (1.73%) displayed a higher anti-HIV activity in cell-free virus when compared to sodium cellulose sulfate, sodium cellulose sulfate-succinate-AZT (17.2%), and the physical mixture of sodium cellulose sulfate and AZT (1.73%). Similarly, Sodium cellulose sulfate-acetate-FLT and the physical mixture of sodium cellulose sulfate-acetate and FLT showed better anti-HIV profile than sodium cellulose sulfate and the mixture of sodium cellulose sulfate and FLT (Table 4). The presence of acetate linker on sodium cellulose sulfate improves the inhibition, possibly by creating new negative charges after hydrolysis of the sodium cellulose sulfate-Acetate-AZT or sodium cellulose sulfate-Acetate-FLT (Table 4).

These conjugates are especially suited for topical microbicidal applications. Cellulose sulfate and other polyanions such as carrageenan, carbopol and naphthalene polymers are currently undergoing or have recently completed clinical efficacy trials for prevention of sexual transmission of HIV. Most of these compounds, however, have shown weak(er) activity against R5 HIV-1 viruses (Dezutti et al, 2004; Moulard et al, 2000). The CS-AZT conjugate also was more effective than AZT against both X4 and R5 HIV-1 viruses. Furthermore, the above-described conjugates present the advantage of not displaying weaker activity against HIV R5 strains (Table 5). Although in weight the conjugate and AZT were similarly potent against cell-free virus, in moles (based on CS~$2\times10^6$ Daltons), the conjugate was 5 orders of magnitude more potent (from µM to subnanomolar). Furthermore, unlike AZT, the conjugate was consistently active against cell-associated HIV.

Substitution of suramin with AZT or FLT improves the anti-HIV activity of suramin by 2-2.5 fold. Furthermore, the physical mixture of suramin and FLT or AZT is at least 55 fold more potent against HIV-1 IIIB than suramin alone, suggesting a positive combinatorial effect (Table 6).

The present invention provides methods of treating, preventing, or reducing transmission of sexually transmitted pathogens. Non-limiting examples of sexually transmitted pathogens include: human immunodeficiency virus (HIV), herpes simplex virus (HSV), human papilloma virus (HPV), *Chlamydia trachomatis* (CT), *Neisseria gonorrhoeae* (NG), and *Haemophilus ducreyi* (HD). The methods of the present invention comprise administering to a person in need of a therapeutically effective amount of the compounds of the present invention or a pharmaceutically acceptable salt thereof.

The compounds of the present invention may be formulated in a wide variety of administration dosage forms and carriers. Topical administration can be delivered vaginally, anally, rectally, over the penis, or over other areas of the body. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip), parenteral, intramuscular, intravenous, subcutaneous, transdermal (which may include a penetration enhancement agent), buccal, nasal, inhalation and suppository administration, among other routes of administration.

In another aspect, this invention provides the composition of matter and the use of the above-described derivatives and conjugates as topical microbicides to treat or prevent sexual transmission of disease, especially HIV/AIDS, chancroid, gonorrhea and chlamydia, herpes and papillomavirus infections.

The compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets, films or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

A typical preparation contains from about 0.01% to about 99% active compound or compounds (w/w). In one embodiment of the present invention, the preparation contains from about 0.1% to about 10% active compound or compounds (w/w). The term "preparation" or "dosage form" is intended to include different formulations of the active compound and one skilled in the art will appreciate that an active ingredient can exist in different preparations depending on the target organ or tissue and on the desired dose and pharmacokinetic parameters.

Solid form preparations include powders, tablets, films, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify. The compounds of the present invention may also be formulated for vaginal administration. Pessaries, tampons, creams, gels, pastes, foams or sprays containing in addition to the active ingredient such carriers as are known in the art to be appropriate. When desired, formulations can be prepared with enteric coatings adapted for sustained or controlled release administration of the active ingredient.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity. All these formulations will contain the amounts of preservatives, such as methyl paraben, propyl paraben benzyl alcohol, benzoic acid, or ascorbic acid, needed to prevent microbial growth.

The term "therapeutically effective amount" as used herein means an amount required to reduce symptoms of the disease in an individual or to prevent primary HIV infections. The dose may be adjusted to the individual requirements in each particular case. That dosage can vary within wide limits depending upon numerous factors such as the severity of the disease to be treated, the age and general health condition of the patient, other medicaments with which the person is being treated, the route and form of administration and the preferences and experience of the medical practitioner involved. One of ordinary skill in treating diseases described herein will be able, without undue experimentation and in reliance on personal knowledge, experience and the disclosures of this application, to ascertain a therapeutically effective amount of the compounds of the present invention for a given disease and patient. For prevention purposes, however, the dosage is likely to be fixed.

In one aspect, the nucleoside analogues and conjugates may be dissolved or dispersed in a number of earners. For example, it may be formulated for "stand alone" usage in forms which include but are not limited to gels, foams, suppositories, creams, lotions, tablets, films, pessaries and the like. Many suitable carriers exist which are well known to those of skill in the art and which may be used in the practice of the present invention. The use of all such carriers is meant to be encompassed by the present invention.

The formulations may further include other ingredients, which are well known to those of skill in the art, including but not limited to stabilizers, colorants, preservatives, perfumes, gelling agents, antioxidants, other active ingredients and the like. The composition of matter of the present invention may contain one or a plurality of nucleoside analogues described above.

In another aspect, the nucleoside analogues and conjugates may be delivered by delivery systems such as rings, rods, diaphragms and other cervicovaginal and rectal devices. Their release may be controlled by the material composing these devices, such as silicone elastomers, ethylene vinyl acetate and polyurethane polymers.

The composition of matter of the present invention may also be used in conjunction with other contraceptive devices. Examples include, but are not limited to, addition to condoms or diaphragms to enhance their activity, or to imbibe a cervico-vaginal sponge that would act as both a mechanical and chemical barrier against sperm and microbicides. The composition of matter may be delivered by a cervical/vaginal device.

In another aspect, the present invention also provides a method of contraception in female mammals, which involves placing a contraceptively effective amount of a spermicidal analogue or conjugate in the vaginal cavity of a female mammal (Table 7). Those of skill in the art will recognize that a variety of means are known by which a compound may be delivered intravaginally, for example, plunger-type applicators, pessaries, tablets, sprays, squeezable tubes, cervical rings, sponges, films and the like. All such means for intravaginal delivery are intended to be encompassed by the present invention. In a preferred embodiment, such conjugates contain cellulose sulfate, polycarboxylic acid or suramin.

Figure 18:
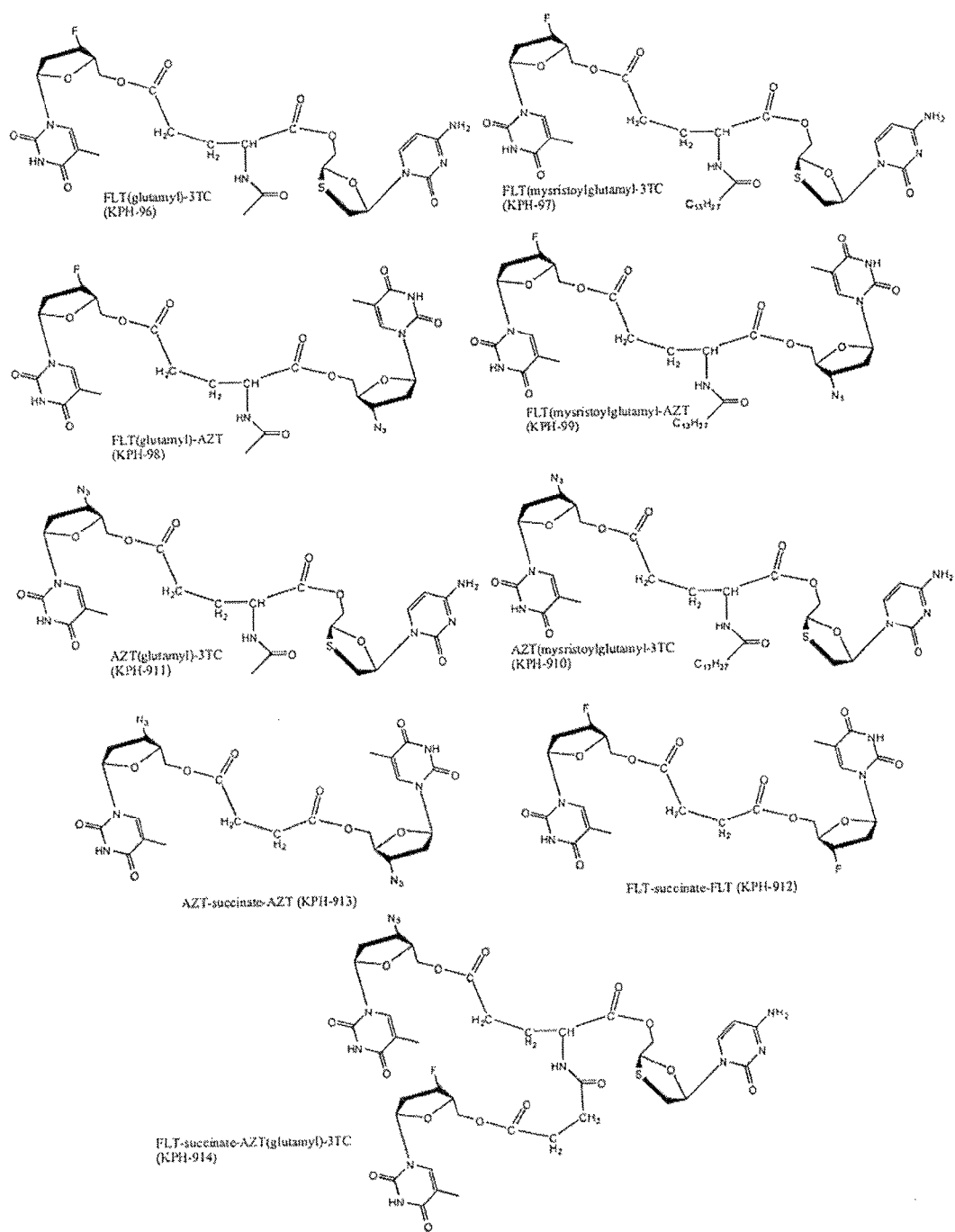
FIG. 18 depicts the chemical structures of some of peptide-nucleoside conjugates with two or three nucleosides and with or without myristic acid.
Figure 19:
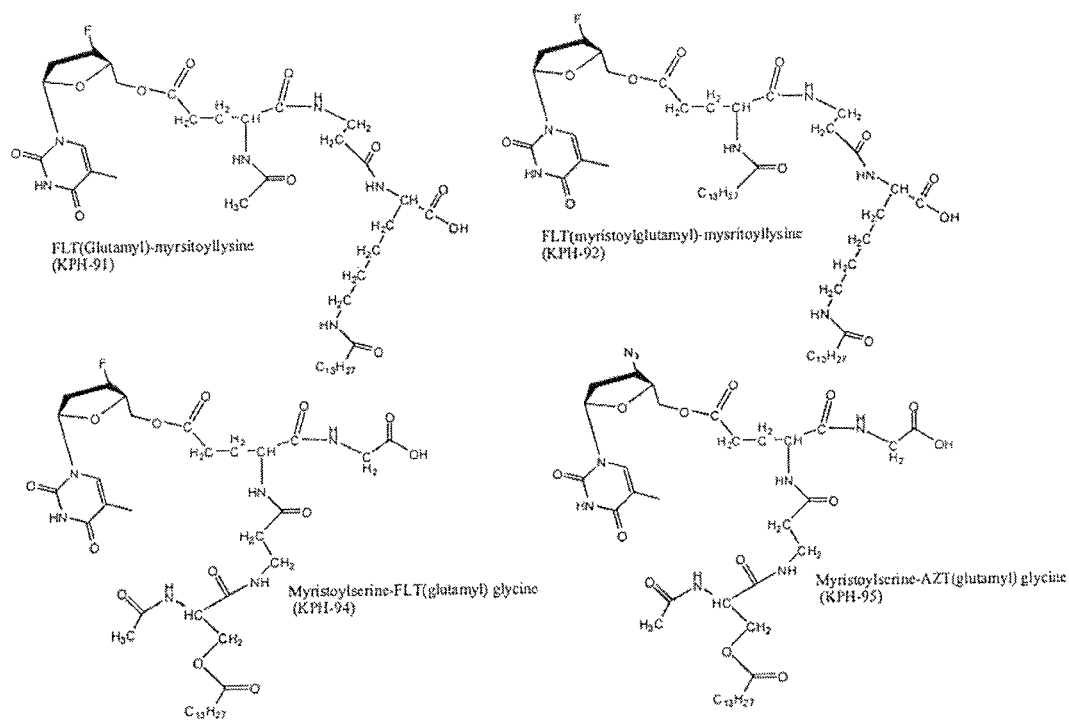
FIG. 19 shows the chemical structures of peptide-nucleoside conjugates containing myristic acid and one nucleoside.

In another aspect, the present invention provides methods of synthesis and possible applications of peptide derivatives containing one to three nucleosides with or without myristic acid analogues (FIGS. 18 and 19). Examples of synthesis of some compounds are given here.

Figure 20:
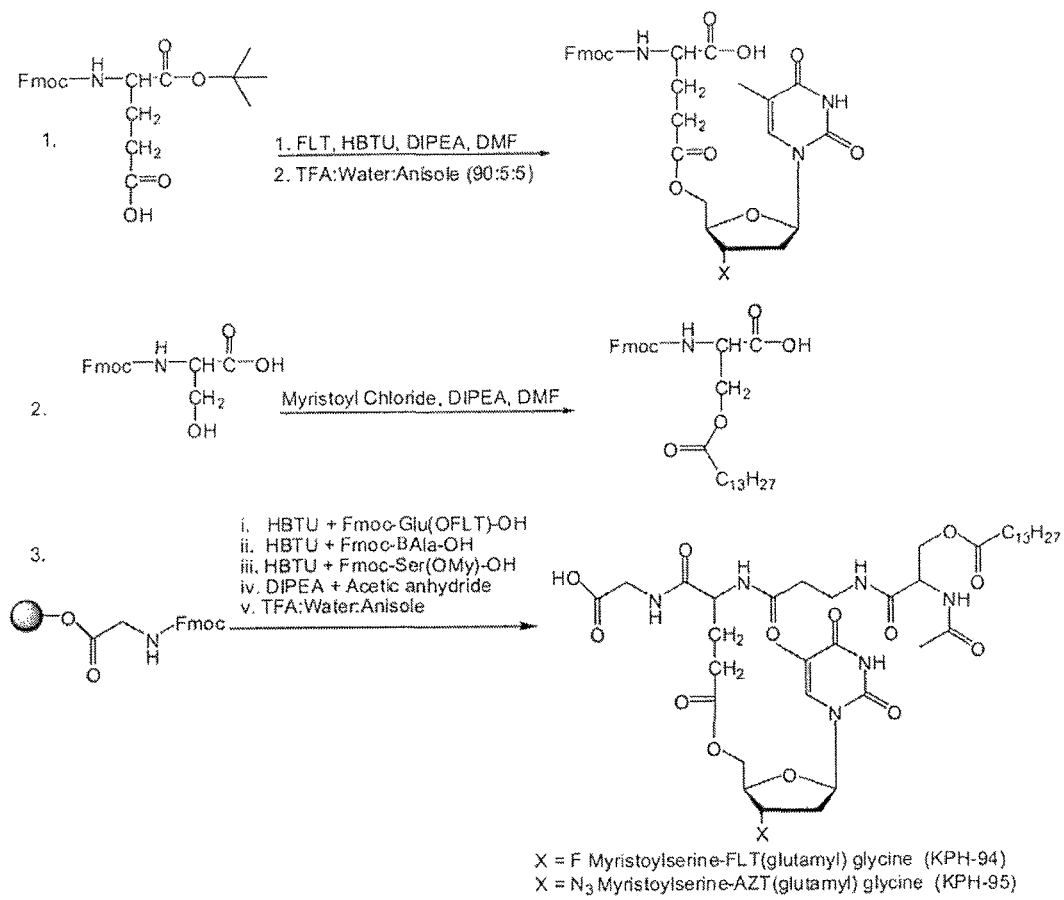
FIG. 20 depicts the synthesis of peptide-nucleoside conjugates containing myristic acid and one nucleoside.

Peptide-nucleoside conjugates containing one nucleoside and myristic acid were synthesized by solid-phase synthesis. For the synthesis of KPH-94 and KPH-95, first Fmoc-Glu(nucleoside)-OH was synthesized as the building block. The reaction of Fmoc-Glu(OH)-tBu with nucleoside in the presence of HBTU and DIPEA, followed by the deprotection of tBu group with TFA afforded the corresponding Fmoc-Glu(nucleoside)-OH. Fmoc-Ser(OMys)OH, a fatty acid building block, was synthesized by the reaction of Fmoc-Ser(OH)—OH with myristoyl chloride in the presence of DIPEA. Solid-phase reaction of building blocks on Fmoc-Gly-Wang resin, followed by cleavage afforded myristoyl-serine-nucleoside(glutamyl)glycine derivatives (KPH-94 and KPH-95) (FIG. 20).

Figure 21:
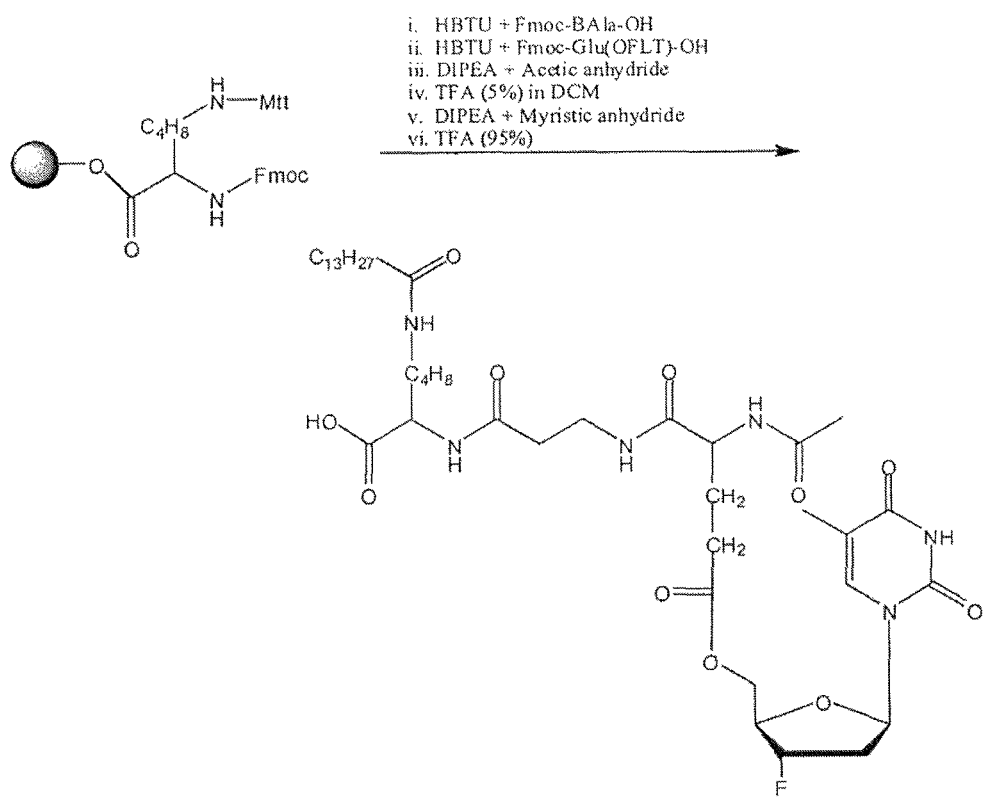
FIG. 21 illustrates the synthesis of FLT(myristoylglutamyl)-mysritoyllysine (KPH-92).

Fmoc-solid-phase peptide protocol was used for the synthesis of KPH-92 and KPH-93 by using Fmoc-Lys-4-methyltrityl (Mtt)-Wang resin, appropriate Fmoc-βAla-OH, Fmoc-Glu(OFLT), acetic anhydride, and myristic anhydride (FIG. 21).

Figure 22:
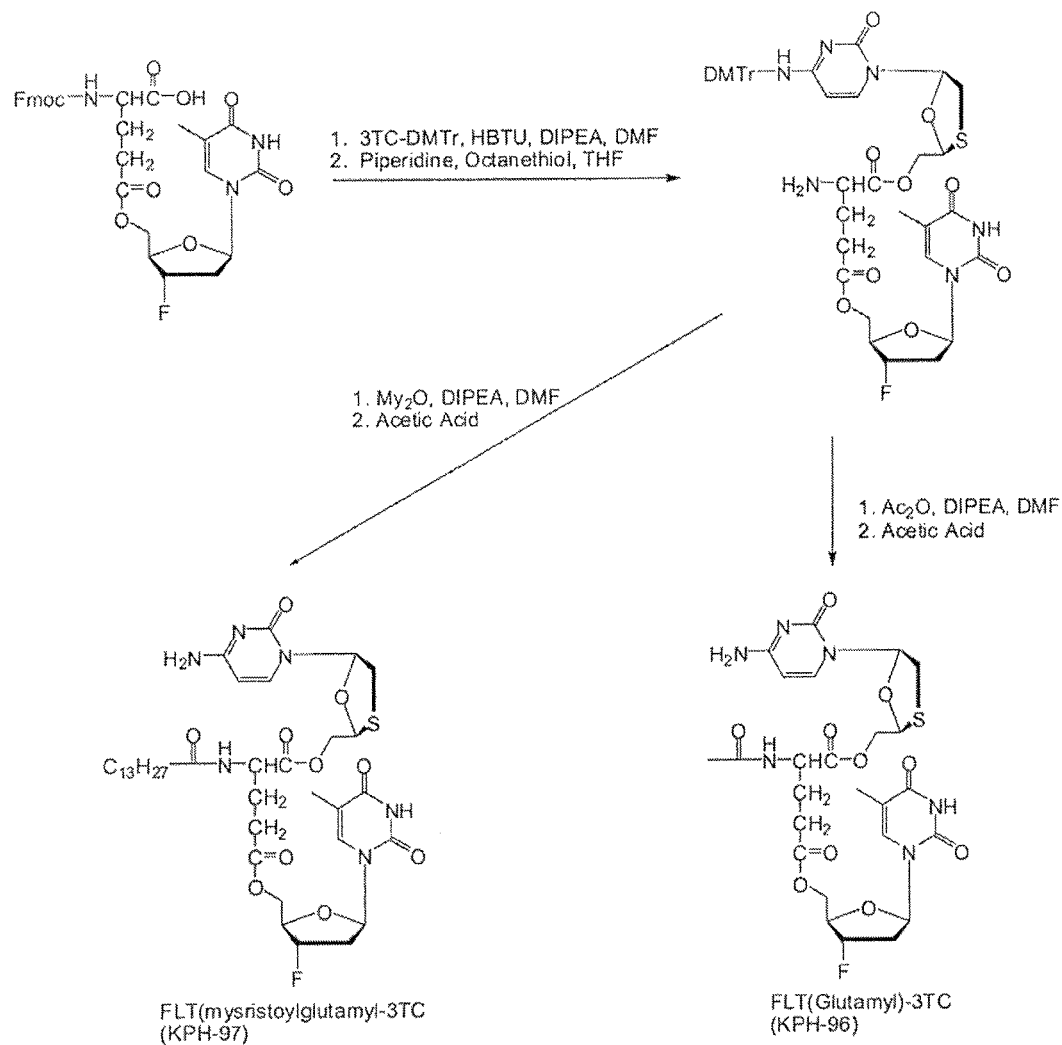
FIGS. 22-24 depict the synthesis of some of peptide-nucleoside conjugates with two or three nucleosides (with or without myristic acid).
Figure 23:
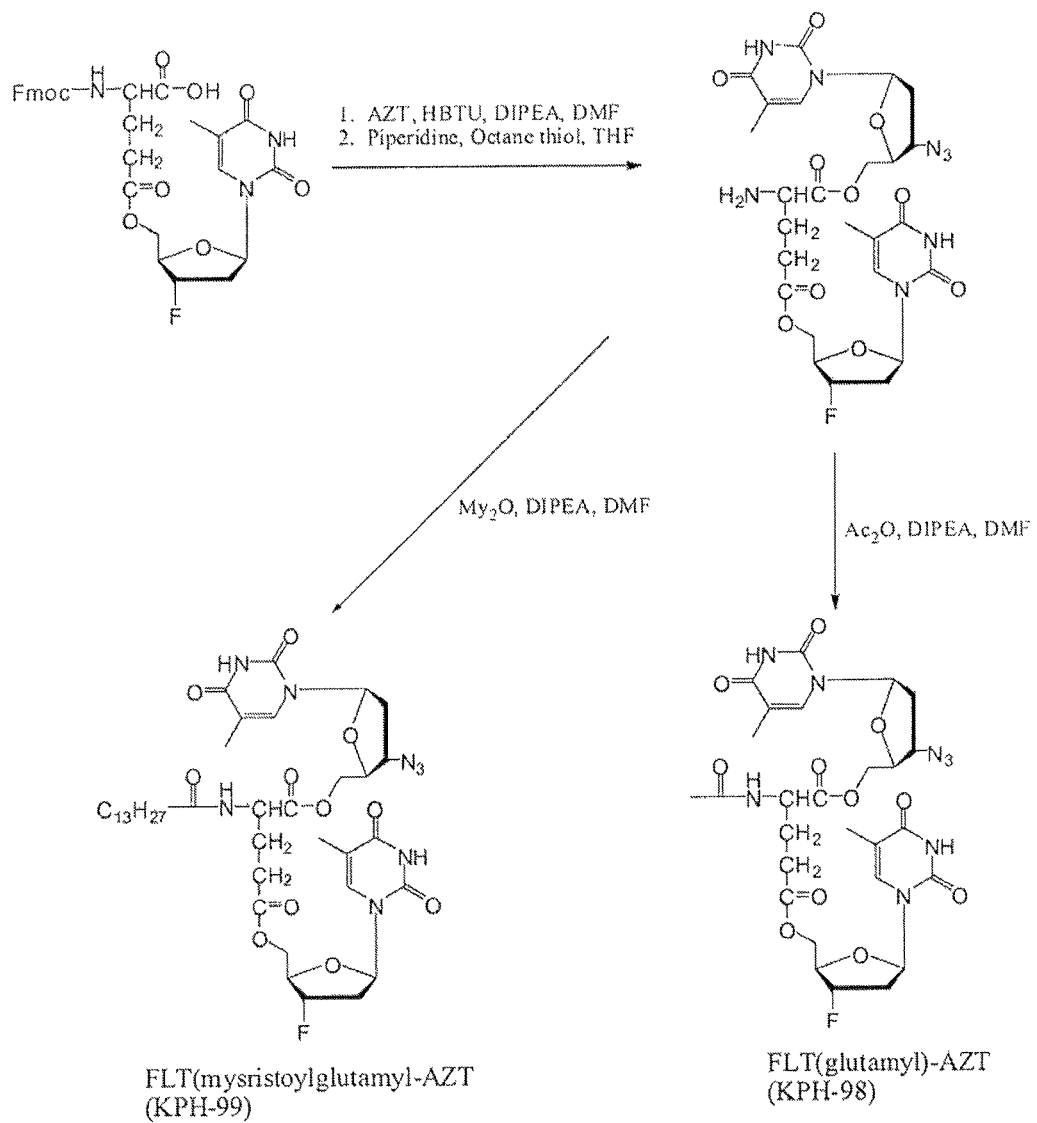
Figure 24:
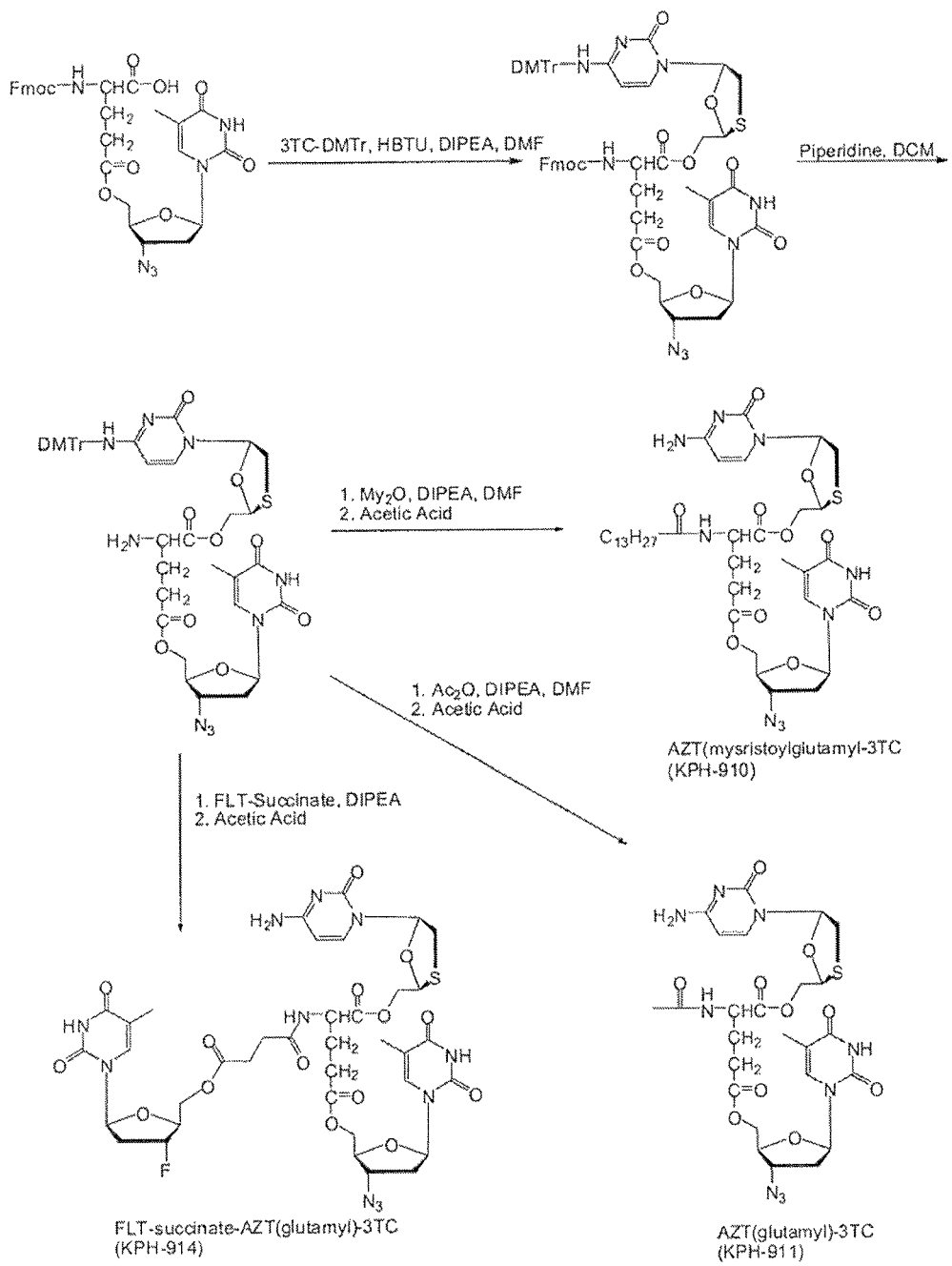

The synthesis of peptides containing two nucleosides and myristate (KPH-97, KPH-99, KPH-910) or acetate (KPH-96, KPH-98, KPH-911) esters was accomplished by the reaction of an appropriate building block, such as Fmoc-Glu(FLT)-OH or Fmoc-Glu(AZT)-OH, with 3TC-DMTr or AZT in the presence of DIPEA, followed by the deprotection of Fmoc group with piperidine and 1-octanethiol, coupling reaction with myristic anhydride or acetic anhydride in the presence of DTPEA, and deprotection of DMTr group with acetic acid (FIGS. 22-24).

For the synthesis of the peptide-containing three nucleosides and myristate ester, $NH_2$-Glu(AZT)-3TC-DMTr was first reacted with FLT-succinate in the presence of DIPEA followed by acetic acid cleavage to afford KPH-914 (FIG. 24).

Peptides conjugated with fatty acids and nucleosides exhibited higher anti-HIV activities when compared with those substituted only with nucleosides. Increasing the number of anti-HIV nucleosides to 2 or 3 on the peptide chain enhanced the anti-HIV potency. Physical mixtures of nucleosides with amino acids and fatty acids used in the conjugation also showed significantly higher potency. The presence of one myristic acid in the conjugates or physical mixtures improved the anti-HIV activity, but addition of two myristic acids to the conjugates was not beneficial (Table 8).

Figure 25:
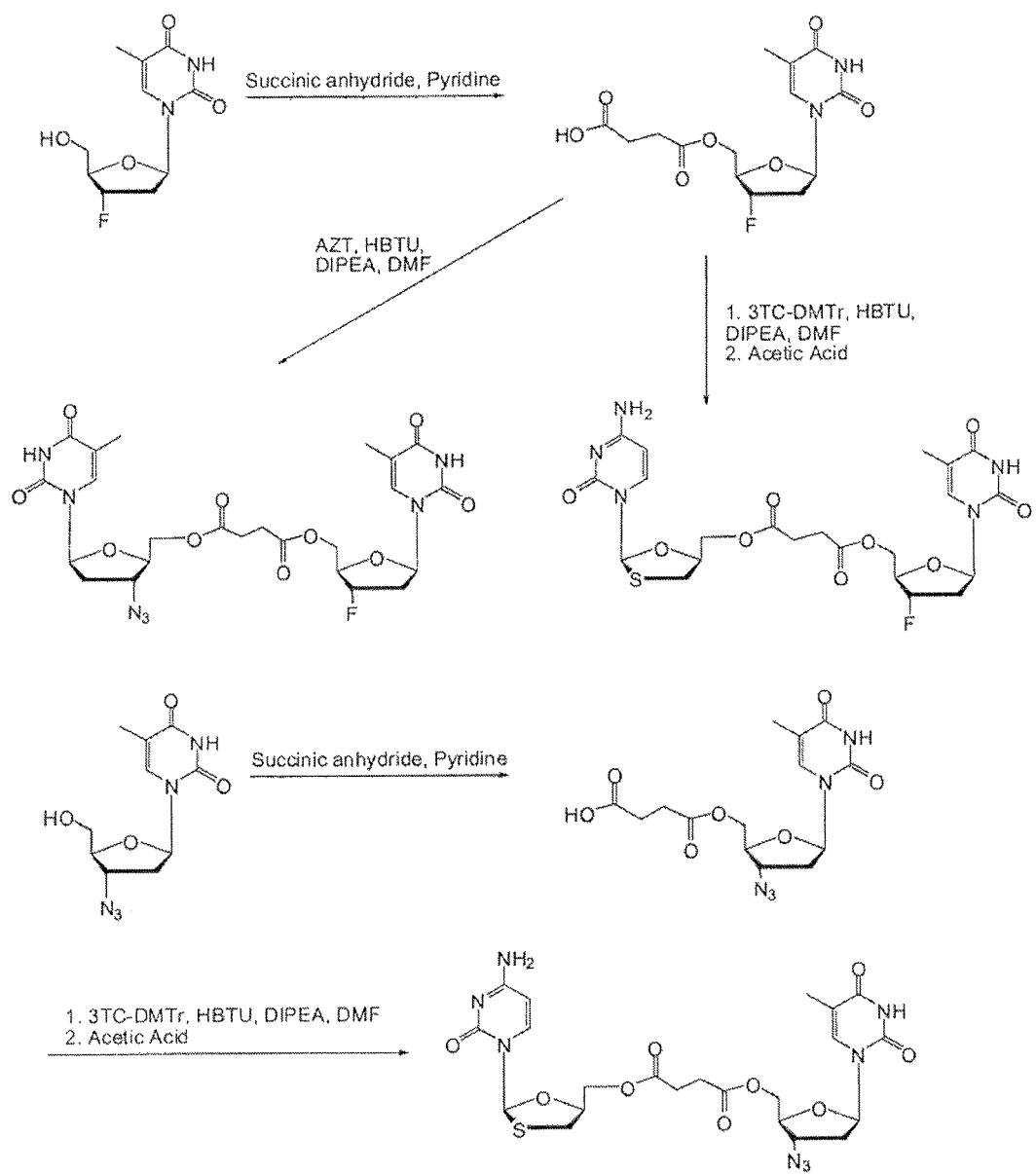
FIG. 25 displays the synthesis of nonsymmetrical nucleoside-nucleoside conjugates using a succinate linker.
Figure 26:
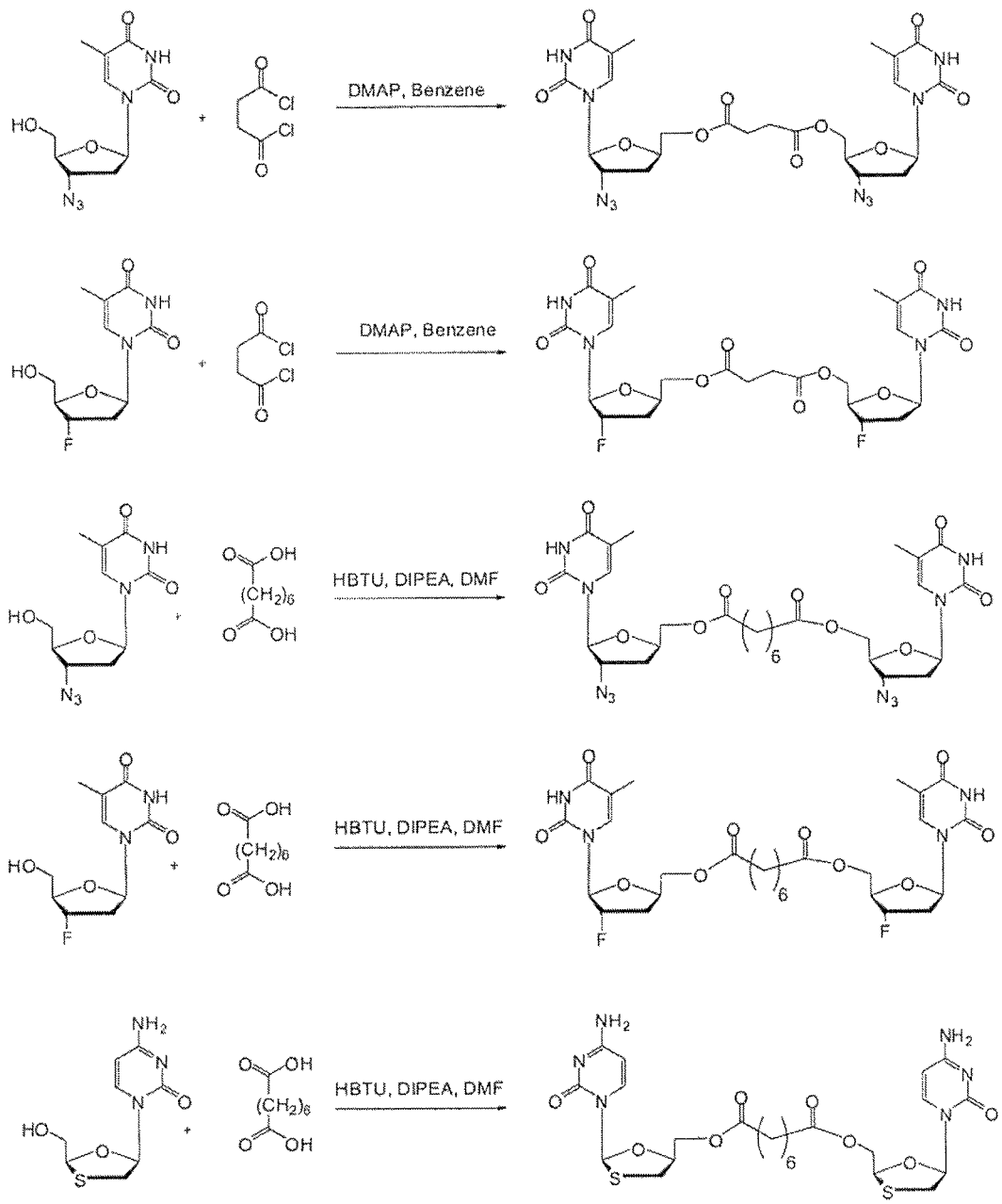
FIG. 26 depicts the synthesis of symmetrical nucleoside-nucleoside conjugates using a succinate or suberate linker.

In another aspect, two anti-HIV nucleosides are linked together through different linkers, such as succinate and suberate. Nucleoside monosuccinates were synthesized from the reaction of nucleosides (e.g., AZT, FLT, 3TC) with succinic anhydride in the presence of pyridine. Nucleoside succinate in DMF was subjected to reaction with the second nucleoside in the presence of HBTU and DIPEA to afford unsymmetrical nucleoside-nucleoside succinate derivatives (FIG. 25). Furthermore, reaction of nucleosides with succinyl chloride in the presence of DMAP or suberic acid in the presence of HBTU and DIPEA afforded symmetrical nucleoside-nucleoside derivatives (FIG. 26).

Figure 27:
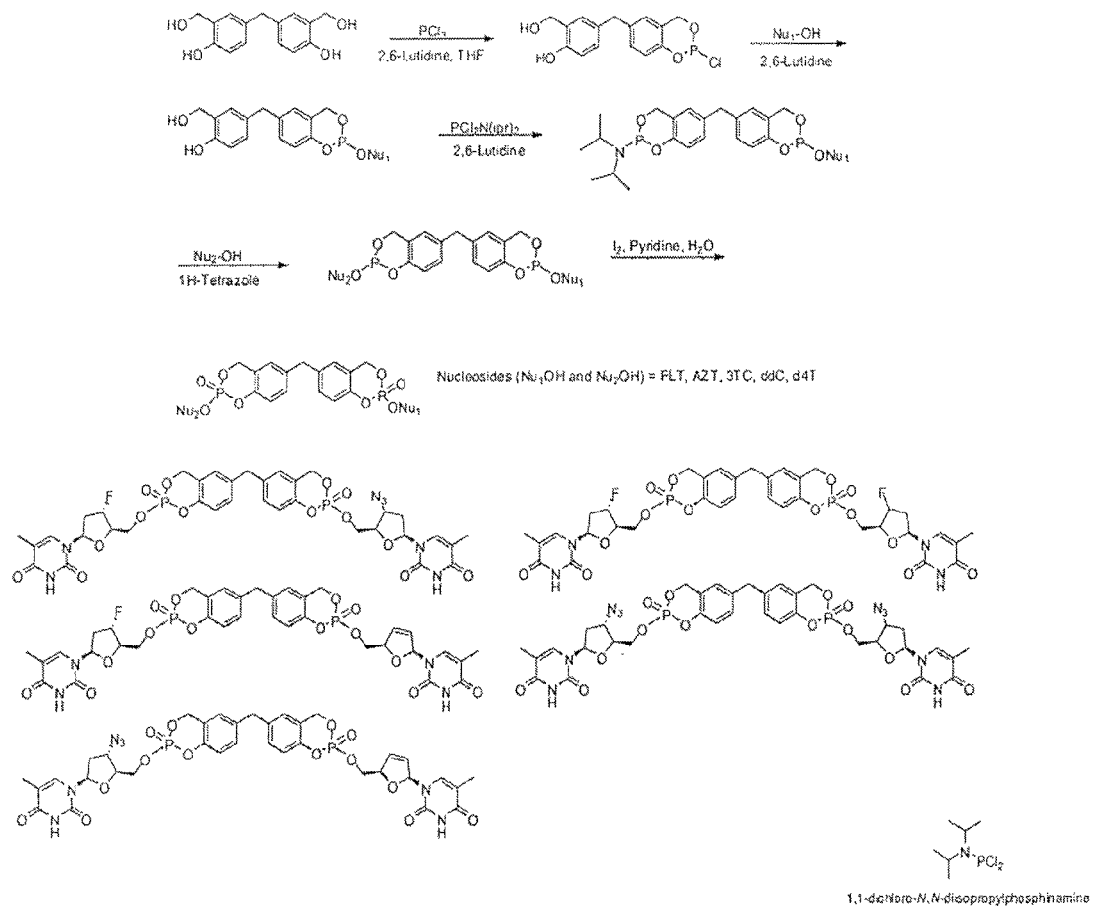
Figure 29:
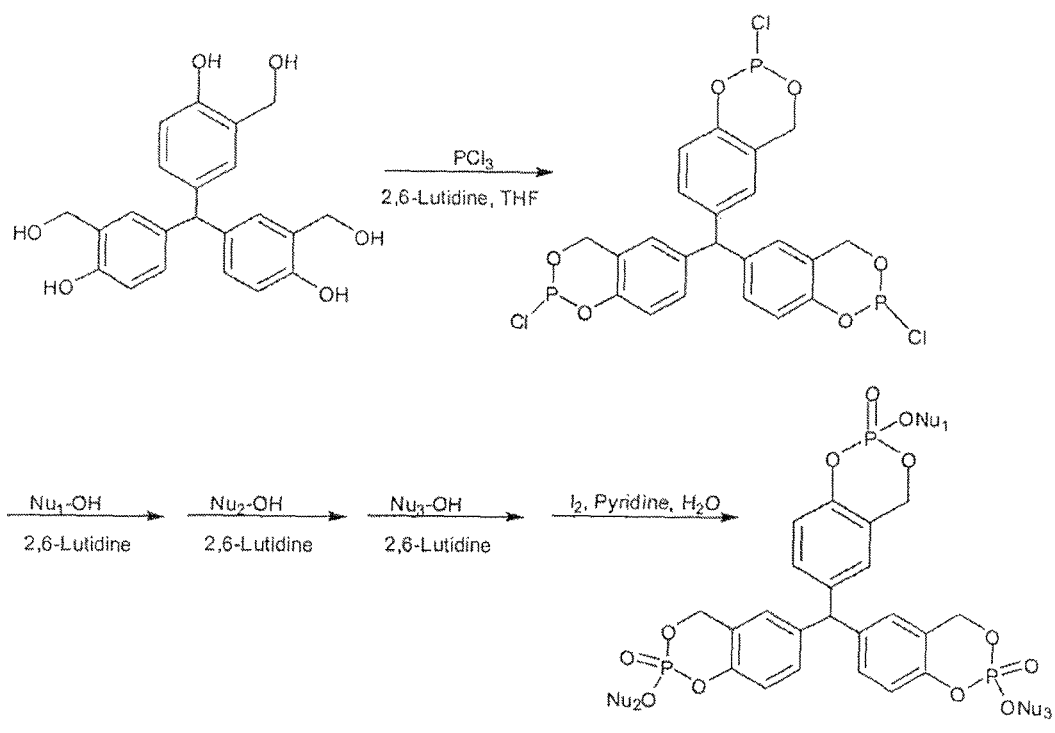
FIG. 29 shows the synthesis of cycloSaligenyl derivatives containing three nucleotides.

In another aspect, two or three anti-HIV nucleosides are linked together through two or three cycloSaligenyl groups substituted on a multivalent ligand. For example, 4,4'-dihydroxy-3,3'-di-(hydroxymethyl)diphenylmethane was reacted with phosphorus trichloride in the presence of 2,6-lutidine. The intermediate was reacted with the first nucleoside, diisopropylphosphoramidous dichloride, and the second nucleoside, respectively. Oxidation reaction afforded dinucleotide dicycloSaligenyl nucleotides (FIG. 27). A similar strategy was used using other multivalent ligands, 4,6-dihydroxy-1,3-benzenedimethanol (FIG. 28) and 4,4',4"-methanetriyltris(2-(hydroxymethyl)phenol) (FIG. 29).

Figure 30:
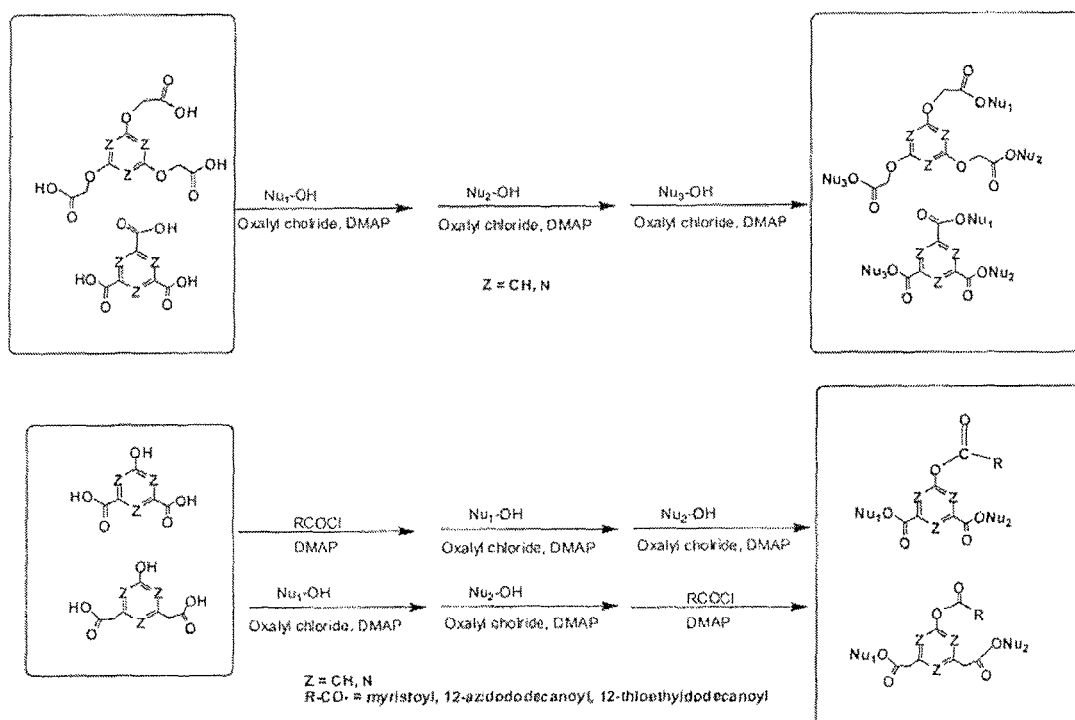
FIG. 30 depicts the synthesis of tricarboxylic acid ester derivatives of nucleosides and fatty acid-dicarboxylic ester conjugates of nucleosides.

In another aspect, two or three anti-HIV nucleosides are linked together through polycarboxylic acids (e.g. tribenzenetriacetic acid, hydroxybenzendicarboxylic acid, [(hydroxyphenylene)dioxy]diacetic acid, tris(carboxymethoxy) benzene, and triazine-tricarboxylic acid derivatives, such as (triazinetriyltroxy)triacetic acid and 1,3,5-triazine-2,4,6-tricarboxylic acid). For example, tricarboxylic acid derivatives were reacted with three nucleosides, respectively, in the presence of a base (e.g., DMAP) and oxalyl chloride to afford tricarboxylic acid derivative substituted with three nucleosides (FIG. 30). Similarly, hydroxydicarboxylic derivatives were substituted with first fatty acid analog and then two nucleosides or two nucleosides first and then with fatty acid analog to produce fatty acid-dinucleoside conjugates (FIG. 30). Appropriate protecting groups for protection of phenol or carboxylic acid groups were used in this sequence.

The present invention also provides a method of neutralizing viral infection, which comprises contact target cells, or overlaying epithelium with a quantity of a compound described above sufficient to neutralize the infection. In a preferred embodiment of the present invention, the virus is HIV.

The present invention also provides a method of inhibiting the growth of a microbe, which comprises contacting the microbe with a quantity of a compound described above sufficient to inhibit the growth of the microbe. Examples of microbes whose growth may be inhibited by the method of the present invention include but are not limited to viruses, bacteria, protozoa, fungi and parasites.

While the invention has been illustrated and described in the FIGS. and foregoing description, the same is to be considered as illustrative and not restrictive in character, it being understood that only the preferred embodiments have been shown and described and that all changes and modifications that come within the spirit of the invention are desired to be protected. In addition, all references and patents cited herein are indicative of the level of skill in the art and hereby incorporated by reference in their entirety.

TABLE 2

Antiviral Activity against multidrug resistant HIV

| Compound Name | Type of Virus | $IC_{50}$ (μg/mL) |
|---|---|---|
| 3'-azido-2',3'-dideoxythymidine | R5 | 0.02 |
| (AZT) | MDR | 0.33 |
| 3'-fluoro-2',3'-dideoxy-5'-O- | R5 | 0.003 |
| (12-azidododecanoyl)thymidine | MDR | 0.003 |
| 3'-fluoro-2',3'-dideoxy-5'-O- | R5 | 0.003 |
| (tetradecanoyl)thymidine | MDR | 0.002 |
| 3'-fluoro-2',3'-dideoxy-5'-O- | R5 | 0.002 |
| (13-thiapentadecanoyl)thymidine | MDR | 0.002 |

$IC_{50}$ = The minimum drug concentration that inhibits HIV-induced cytopathic effect by 50%, calculated by using a regression analysis program for semilog curve fitting. Assay endpoint = RT activity
HIV-1 clinical isolates: R5 = 92TH014; MDR = Multidrug resistant virus 7324-1. Assay endpoint = RT level. Compound-virus-cell incubation = 6 h. After removing supernatant, cells were further incubated for 6 days.

TABLE 1

Anti HIV-1 Activity of Fatty Acid Substituted Nucleoside Derivatives

| | Cell-Free Virus | | Cell-Associated Virus |
|---|---|---|---|
| Compound Name | IIIB | BaL | SupT1 (IIIB) |
| 3'-azido-2',3'-dideoxythymidine (AZT) | 9.2 | 0.8 | >100 |
| 3'-azido-2',3'-dideoxy-5'-O-(9-thiatertradecanoyl)thymidine | 3.7 | 8.1 ( | 42.0 |
| 3'-azido-2',3'-dideoxy-5'-O-(11-thioethylundecanoyl)thymidine | 3.8 | 2.6 | 44.9 |
| 3'-azido-2',3'-dideoxy-5'-O-(12-bromododecanoyl)thymidine | 5.6 | 2.6 | >100 |
| 3'-azido-2',3'-dideoxythymidine (AZT) + 12-bromododccanoic acid | 19 | 4.8 | >100 |
| 3'-azido-2',3'-dideoxy-5'-O-(tetradecanoyl)thymidine | 1.5 | 2.4 | >100 |
| 3'-azido-2',3'-dideoxy-5'-O-(tetradecyl)thymidine (ether derivative) | 57.8 | 12.8 | >100 |
| 3'-azido-2',3'-dideoxythymidine (AZT) + tetradecanoic acid | 0.7 | 22.9 | >100 |
| 3'-azido-2',3'-dideoxy-5'-O-(pentadecanoyl)thymidine | 8.8 | 2.2 | >100 |
| 3'-fluoro-2',3'-deoxythymidine (FLT) | 0.2 | 0.1 | >100 |
| 3'-fluoro-2',3'-dideoxy-5'-O-(12-bromododecanoyl)thymidine | 0.9 | <0.1 | >100 |
| 3'-fluoro-2',3'-dideoxy-5'-O-(9-thiatertradecanoyl)thymidine | 5.4 | 2.1 | >100 |
| 3'-fluoro-2',3'-dideoxy-5'-O-(2-methoxytctradccanoyl)thymidine | 0.5 | 0.1 | >100 |
| 3'-fluoro-2',3'-dideoxy-5'-O-(12-azidododecanoyl)thymidine | 0.4 | 0.2 | 5.9 |
| 3'-fluoro-2',3'-dideoxy-5'-O-(tetradecanoyl)thymidine | 0.3 | 0.5 | 2.9 |
| 3'-fluoro-2',3'-dideoxy-5'-O-(tetradecyl)thymidine (ether derivative) | 79.1 | 77.3 | >100 |
| 3'-fluoro-2',3'-dideoxythymidine (AZT) + tetradecanoic acid | 0.1 | 0.4 | 15.6 |
| 3'-fluoro-2',3'-dideoxy-5'-O-(13-thiapentadecanoyl)thymidine | 0.5 | <0.1 | 1.1 |
| 3'-fluoro-2',3'-dideoxy-5'-O-(12-aminododecanoyl)thymidine | 0.67 | | |
| 3'-fluoro-2',3'-dideoxy-5'-O-(12-(N-5(6)carboxylfluoresceinamino-dodecanoyl)thymidine | 4.3 | | |
| 2',3'-dideoxy-3'-thiacytidine (lamivudine, 3TC) | 7.5 | 2.6 | 18.4 |
| N4, 5'-O-dimyristoyl-2',3'-dideoxy-3'-thiacytidine | >100 | 87.8 | >100 |
| N4, 5'-O-di(12-azidododecanoyl)-2',3'-dideoxy-3'-thiacytidine | >100 | 49.1 | >100 |
| N4-tetradecanoyl-2',3'-dideoxy-3'-thiacytidine | 4.8 | 0.3 | 0.3 |
| N4-(12-azidodccanoyl)-2',3'-dideoxy-3'-thiacytidine | 13.3 | 1.7 | 6.6 |
| N4-(13-thiapentadecanoyl)-2',3'-dideoxy-3'-thiacytidine | 2.5 | 0.2 | >100 |
| 5'-O-tetradecanoyl-2',3'-dideoxy-3'-thiacytidine | 0.3 | 0.082 | 27.3 |
| 5'-O-(12-azidododecanoyl)-2',3'-dideoxy-3'-thiacytidine | 0.88 | 0.08 | >100 |
| 5'-O-(13-thiapentadecanoyl)-2',3'-dideoxy-3'-thiacytidinec | 1.1 | <0.1 | >100 |
| 2',3'-didehydro-2',3'-dideoxythymidine (d4T) | 6.0 | 6.3 | 30.5 |
| 5'-O-myristoyl-2',3'-didehydro-2',3'-dideoxythymidine | 34 | 5.4 | >100 |
| 5'-O-(12-azidodocanoyl)-2',3'-didehydro-2',3'-dideoxythymidine | 3.0 | 1.4 | 10.0 |
| 5'-O-(12-thiocthylazidodccanoyl)-2',3'-didchydro-2',3'-dideoxythymidine | 6.7 | 2.7 | 21.7 |
| 12-bromododecanoyl-2',3'-didehydro-2',3'-dideoxythymidine | 7.2 | 1.1 | >100 |
| 2',3'-dideoxy-5-fluoro-3'-thiacytidine (emtricitabine, FTC) | 0.48 | 0.18 | 21.9 |
| 5'-O-(12-azidododecanoyl)-2',3'-dideoxy-5-fluoro-3'-thiacytidine | 0.39 | 0.11 | 4.3 |
| 5'-O-tetradecanoyl-2',3'-dideoxy-5-fluoro-3'-thiacytidine | 0.056 | 0.033 | 1.7 |
| 5'-O-(13-thiapentadecanoyl)-2',3'-dideoxy-5-fluoro-3'-thiacytidine | 0.024 | 0.02 | 2.4 |
| 2',3'-dideoxy-5-fluoro-3'-thiacytidine (emtricitabine, FTC) + myristic acid | 0.6 | 0.1 | 9.9 |
| 2',3'-dideoxy-5-fluoro-3'-thiacytidine (emtricitabine, FTC) + 12-thioethydodecanoic acid (13-thiapentadecanoic acid) | 0.1 | 0.2 | 9.8 |

Data represent $IC_{50}$ (50% inhibitory concentration) and are expressed in μg/mL. Single-round infection assay where compounds, virus and cells were incubated for 2 hours. Cells were then washed and cultured for additional 48 h. Infection was measured by HIV-LTR driven Galactosidase expression.

TABLE 3

Antibacterial Activity against *Haemophilus ducreyi*

| Compound Name | H. ducreyi Strain | | |
|---|---|---|---|
| | HMC56 | HMC 62 | HMC 64 |
| 3'-fluoro-2',3'-dideoxy-5'-O-(13-thiapentadecanoyl)thymidine | 125 | 125 | 125 |
| 3'-fluoro-2',3'-dideoxy-5'-O-(12-azidododecanoyl)thymidine | 500 | 125 | 125 |
| 3'-azido-2',3'-dideoxy-5'-O-(9-thiatertradecanoyl)thymidine | 250 | 250 | 750 |
| 3'-azido-2',3'-dideoxythymidine (AZT) | 125 | 750 | 500 |

Data represent MIC (minimum inhibitory concentration) and are expressed in μg/mL

TABLE 4

Anti HIV Activity of Cellulose Sulfate-3'-Azido-2',3'-dideoxythymidine and Cellulose Sulfate-3'-Fluoro-2',3'-dideoxythymidine Conjugates

| Compound | Chemical Name | Cytotoxicity | Cell-FreeVirus | | Cell-Associated Virus |
|---|---|---|---|---|---|
| | | | IIIB | BaL | Sup T1-IIIB |
| CS | Sodium Cellulose Sulfate | >100 | 5.9 | 62.5 | 2.5 |
| CS-Ac | Sodium Cellulose Sulfate-Acetate | >100 | 1.27 | 1.81 | 6.57 |
| AZT | 3'-azido-2',3'-dideoxythymidine | >100 | 2.4 | 4.2 | >100 |
| CS-Ac-AZT | Sodium Cellulose Sulfate-Acetate-AZT (1.73%) | >100 | 2.5 | 8.1 | 5.6 |
| CS-Ac + AZT | Sodium cellulose sulfate-Acetate + AZT (1.73%) | >100 | 1.7 | 2.5 | 8.0 |
| CS-Suc-AZT | Sodium cellulose sulfate-succinate-AZT (17.2%) | >100 | 2.2 | 9.9 | 74.8 |
| CS + AZT | Sodium cellulose sulfate + AZT (1.73 %) | >100 | 16.2 | 15.3 | 7.6 |
| CS-Ac-FLT | Sodium Cellulose Sulfate-Acetate-FLT (1.45%) | >100 | 2.3 | 1.5 | 5.8 |
| CS-Ac + FLT | Sodium cellulose sulfate-Acetate + FLT (1.26%) | >100 | 0.72 | 0.31 | 4.72 |
| CS + AZT | Sodium cellulose sulfate + FLT (1.25 %) | >100 | 6.2 | 7.1 | 7.4 |

Data represent $EC_{50}$ (50% effective concentration) and are expressed in μg/mL

TABLE 5

Antiviral Activity of 3'-Azido/3'-Fluoro-2',3'-dideoxythymidine-Cellulose Sulfate Conjugates Against R5 and Multidrug Resistant HIV-1 Clinical Isolates

| Compound Name | Type of Virus | $IC_{50}$ (μg/mL) |
|---|---|---|
| Cellulose Sulfate-Acetate-AZT | R5 | 3.52 |
| | MDR | 4.22 |
| Cellulose Sulfate-Acetate-FLT | R5 | 2.67 |
| | MDR | 0.50 |
| Cellulose Sulfate (CS) | R5 | >20.0 |
| | MDR | 1.61 |
| Dextran Sulfate | R5 | 15.7 |
| | MDR | 3.12 |

Assay endpoint = p24 level (ELISA). Compound-virus-cell incubation = 6 h. After removing supernatant, cells were further incubated for 6 days.

$IC_{50}$ = The minimum drug concentration that inhibits HIV-induced cytopathic effect by 50%, calculated by using a regression analysis program for semilog curve fitting HIV-1 clinical isolates: R5 = 92TH014; MDR = Multidrug resistant virus 7324-1

TABLE 6

Anti HIV Activity of Suramin-3'-Azido-2',3'-dideoxythymidine and Suramin-3'-Fluoro-2',3'-dideoxythymidine Conjugates

| Compound | Chemical Name | Cytotoxicity | Cell-FreeVirus | |
|---|---|---|---|---|
| | | | IIIB | BaL |
| Suramin | Suramin | >100 | 49.1 | 1.0 |
| Suramin-AZT | Suramin-3'-azido-2',3'-dideoxythymidine | >100 | 19.4 | 7.3 |
| Suramin | AZT | Suramin | AZT (45:55) | >100 | 0.9 | 1.4 |
| Suramin-FLT | Suramin-3'-fluoro-2',3'-dideoxythymidine | >100 | 23.6 | 6.2 |
| Suramin + FLT | Suramin + FLT (47:53) | >100 | 0.4 | <0.1 |

Data represent $EC_{50}$ (50% effective concentration) and are expressed in μg/mL

TABLE 7

Contraceptive efficacy of 3'-Azido-2',3'-dideoxythymidine-Cellulose Sulfate conjugate

| Group | Concentration (mg/ml) | No. of Pregnant females/total | Pregnancy rate (%) |
|---|---|---|---|
| TALP | Control | 4/4 | 100 |
| CS | 1 mg/ml | 0/5 | 0 |
| AZT-CS | 1 mg/ml | 0/5 | 0 |

Female rabbits were inseminated with pooled rabbit semen containing 1 mg/mL of test compound or medium control (TALP)

TABLE 8

Anti HIV Activity of Peptide Conjugates of Nucleosides with or without Fatty Acid Substitution

| Compound | Chemical Name | Cyto-toxicity μg/mL. | Cell-free HIV-1 (IIIB) μg/mL. | Cell-free HIV-1 (IIIB) μM |
|---|---|---|---|---|
| | 3'-azid-2',3'-dideoxythymidine (AZT) | >100 | 9.2 | 34.4 |
| | 3'-fluoro-2',3'-deoxythymidine (FLT) | >100 | 0.2 | 0.8 |
| | 2',3'-dideoxy-3'-thiacytidine (lamivudine, 3TC) | >100 | 7.5 | 32.7 |
| KPH-96 | FLT(Glutamyl)-3TC | >100 | 10.7 | 17.1 |
| KPH-97 | FLT(mysristoylglutamyl-3TC | >100 | 1.6 | 2.0 |
| KPH-921 | FLT + 3TC + Glutamic acid | >100 | 0.6 | |
| KPH-922 | FLT + 3TC + Glutamic acid + Myristic acid | >100 | 0.3 | |
| KPH-98 | FLT(Glutamyl)-AZT | >100 | 9.0 | 13.5 |
| KPH-99 | FLT(mysristoylglutamyl-AZT | >100 | 2.0 | 2.4 |
| KPH-923 | FLT + AZT + Glutamic acid | >100 | 1.0 | |
| KPH-924 | FLT + AZT + Glutamic acid + Myristic acid | >100 | 0.3 | |
| KPH-911 | AZT(Glutamyl)-3TC | >100 | 7.8 | 12.0 |
| KPH-910 | AZT(mysristoylglutamyl-3TC | >100 | 4.9 | 6.0 |
| KPH-919 | AZT + 3TC + Glutamic acid | >100 | 1.7 | |
| KPH-920 | AZT + 3TC + Glutamic Acid + Myristic Acid | >100 | 1.9 | |
| KPH-913 | AZT-succinate-AZT | >100 | 8.6 | 13.9 |
| KPH-912 | FLT-succinate-FLT | >100 | 2.1 | 3.7 |
| KPH-914 | FLT-Succinate-AZT(glutamyl)-3TC | >100 | 0.9 | 0.96 |
| KPH-928 | FLT-Succinate + AZT + 3TC + Glutamic acid | >100 | 1.8 | |
| KPH-926 | FLT + AZT + 3TC + Glutamic acid | >100 | 0.8 | |
| KPH-927 | FLT + AZT + 3TC + glutamic acid + Myristic acid | >100 | 0.3 | |
| KPH-91 | FLT(Glutamyl)-myrsitoyllysine | >100 | 8.7 | 10.5 |
| KPH-92 | FLT(myristoylglutamyl)-mysritoyllysine | >100 | 24.7 | 26.8 |
| KPH-94 | Myristoylserine-FLT (glutamyl) glycine | >100 | 9.3 | 11.1 |
| KPH-95 | Myristoylserine-AZT (glutamyl) glycine | >100 | 54.5 | 63.1 |

Data represent $EC_{50}$ (50% effective concentration). Single-round infection assay where compounds, virus and cells were incubated for 2 hours. Cells were then washed and cultured for additional 48 h. Infection was measured by HIV-LTR driven Galactosidase expression.

The invention claimed is:

1. A compound comprising at least one substituted nucleoside of Formula III:

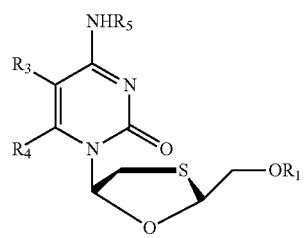

wherein
$R_1$=H;
$R_3$=H, Br, I, F, Cl, alkyl, alkene, alkyne, aryl, O-alkyl, O-aryl;
$R_4$=H, Br, I, F, Cl, alkyl, alkene, alkyne, aryl, O-alkyl, O-aryl; and
$R_5$=Z—CO—, an anionic polymer complexed with a cleavable linker, a fatty acid analogue complexed with a cleavable linker, a fatty alcohol analogue complexed with a cleavable linker, a carboxylic ester side chain of a linear or cyclic peptide, a polycarboxylic ester aryl or heteroaryl, carbopol, or a phosphodiester; wherein
the fatty acid analogue is selected from the group consisting of $X'(CH_2)_nY'(CH_2)_nCO$— and $CH_3(CH_2)_nCH(Br)CO$—; and
the fatty alcohol analogue is selected from the group consisting of $X'(CH_2)_nY'(CH_2)_nCH_2O$— and $CH_3(CH_2)_nCH(Br)CH_2O$—;
Z =suramin, cellulose acetate, or an anionic polymer;
$X'$=$CH_3$, $N_3$, alkyl-S, alkyl-O, aryl-O, aryl-S, alkyl-NH, aryl-NH, Br, Cl, F, I, OH, $NH_2$, COOH, CHO, $CH_3S$, aryl, heteroaryl, phenyl, substituted phenyl, suramin, cellulose acetate, or an anionic polymer;
$Y'$=$CH_2$, O, S, NH;
independently, n =0-18.

2. The compound according to claim 1, wherein the substituted nucleoside exhibits microbicide activity to treat infection or reduce transmission of a sexually transmitted pathogen.

3. The compound according to claim 2, wherein the sexually transmitted pathogen is at least one selected from human immunodeficiency virus (HIV), herpes simplex virus (HSV), human papilloma virus (HPV), *Chlamydia trachomatis* (CT), *Neisseria gonorrhoeae* (NG), and *Haemophilus ducreyi* (HD).

4. A pharmaceutical composition comprising an effective amount of at least one compound according to claim 1, in combination with a pharmaceutically acceptable carrier, additive or excipient.

5. The pharmaceutical composition according to claim 4, wherein the composition is in the form of a solution, suspension, capsule, tablet, film, pessary, gel, cream, ointment, or spray.

6. A method of reducing transmission of a sexually transmitted pathogen, comprising administering to a person in need of a therapeutically effective amount of the compound according to claim 1 or a pharmaceutically acceptable salt thereof.

7. The method of claim 6, wherein the sexually transmitted pathogen is at least one selected from human immunodeficiency virus (HIV), herpes simplex virus (HSV), human papilloma virus (HPV), *Chlamydia trachomatis* (CT), *Neisseria gonorrhoeae* (NG), and *Haemophilus ducreyi* (HD).

8. The method of claim 7, wherein the sexually transmitted pathogen is HIV.

9. The method according to claim 6, wherein the compound is administered via or applied to a mucous membrane.

10. A method of treating infection or reducing transmission of a sexually transmitted pathogen, comprising administering to a person in need of a therapeutically effective amount of the compound according to claim 1 or a pharmaceutically acceptable salt thereof.

11. The method of claim 10, wherein the sexually transmitted pathogen is at least one selected from human immunodeficiency virus (HIV), herpes simplex virus (HSV), human papilloma virus (HPV), *Chlamydia trachomatis* (CT), *Neisseria gonorrhoeae* (NG), and *Haemophilus ducreyi* (HD).

12. The method of claim 11, wherein the sexually transmitted pathogen is HIV.

13. The method according to claim 12, wherein the compound is administered via or applied to a mucous membrane.

14. A compound comprising at least one substituted nucleoside of Formula III:

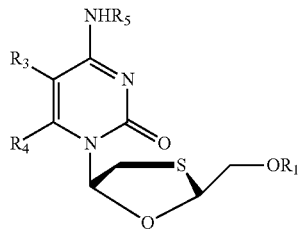

wherein
$R_1$=H
$R_3$=H
$R_4$=H;
$R_5$=$CH_3(CH_2)_{12}CO-$, or $N_3(CH_2)_{11}CO-$, or $CH_3CH_2S(CH_2)_{11}CO-$.

* * * * *